US008652825B2

(12) United States Patent
Eiteman et al.

(10) Patent No.: US 8,652,825 B2
(45) Date of Patent: *Feb. 18, 2014

(54) MICROBIAL PRODUCTION OF PYRUVATE AND OTHER METABOLITES

(75) Inventors: Mark A. Eiteman, Athens, GA (US); Elliot Altman, Rockvale, TN (US)

(73) Assignee: University of Georgia Research Foundation, Inc., Athens, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/584,471

(22) Filed: Aug. 13, 2012

(65) Prior Publication Data

US 2013/0045512 A1    Feb. 21, 2013

Related U.S. Application Data

(63) Continuation of application No. 12/825,059, filed on Jun. 28, 2010, now Pat. No. 8,278,076, which is a continuation-in-part of application No. 10/923,458, filed on Aug. 20, 2004, now Pat. No. 7,749,740, which is a continuation-in-part of application No. PCT/US03/05083, filed on Feb. 20, 2003.

(60) Provisional application No. 60/359,279, filed on Feb. 20, 2002, provisional application No. 60/402,747, filed on Aug. 12, 2002, provisional application No. 61/274,252, filed on Aug. 14, 2009.

(51) Int. Cl.
| | |
|---|---|
| *C12P 13/06* | (2006.01) |
| *C12P 7/40* | (2006.01) |
| *C12N 9/00* | (2006.01) |
| *C12N 9/04* | (2006.01) |
| *C12N 1/20* | (2006.01) |
| *C12N 15/00* | (2006.01) |
| *C07H 21/04* | (2006.01) |

(52) U.S. Cl.
USPC ........ 435/252.3; 435/116; 435/136; 435/183; 435/190; 435/320.1; 536/23.2

(58) Field of Classification Search
None
See application file for complete search history.

(56) References Cited

U.S. PATENT DOCUMENTS

| | | | |
|---|---|---|---|
| 3,458,400 | A | 7/1969 | Ichiro et al. |
| 4,326,030 | A | 4/1982 | El-Sayed |
| 5,225,593 | A | 7/1993 | Imanari et al. |
| 5,559,016 | A | 9/1996 | Katsumata et al. |
| 5,643,779 | A | 7/1997 | Ehrlich et al. |
| 5,888,783 | A | 3/1999 | Tomita et al. |
| 5,916,781 | A | 6/1999 | Yamamoto et al. |
| 6,214,591 | B1 | 4/2001 | Tomita et al. |
| 7,256,021 | B2 | 8/2007 | Hermann |
| 7,749,740 | B2 * | 7/2010 | Eiteman et al. ............. 435/136 |
| 8,278,076 | B2 * | 10/2012 | Eiteman et al. ............. 435/116 |
| 2004/0115780 | A1 | 6/2004 | Hermann |

FOREIGN PATENT DOCUMENTS

| | | |
|---|---|---|
| DE | 197 43 894.6 | 10/1997 |
| DE | 101 29 711 A1 | 1/2003 |
| DE | 102 20 234 A1 | 11/2003 |
| DE | 103 12 775 A1 | 10/2004 |
| DE | 101 29 711 B4 | 8/2007 |
| DE | 103 12 775 B4 | 11/2007 |
| EP | 0 389 620 A1 | 10/1990 |
| EP | 0 937 774 A1 | 8/1999 |
| JP | 62036196 A2 | 2/1987 |
| WO | WO 99/18228 A2 | 4/1999 |
| WO | WO 99/18228 A3 | 5/1999 |
| WO | WO 99/53035 A1 | 10/1999 |
| WO | WO 01/92556 A1 | 12/2001 |
| WO | WO 03/000913 A2 | 1/2003 |
| WO | WO 03/000913 A3 | 5/2003 |
| WO | WO 03/070913 A2 | 8/2003 |
| WO | WO 03/093488 A1 | 11/2003 |
| WO | WO 03/070913 A3 | 10/2004 |

OTHER PUBLICATIONS

Yu et al. Microbiology. Feb. 2001;147(Pt 2):431-8.*
Flores et al. FEBS Lett. Aug. 4, 1997;412(3):531-4.*
Aceti et al., "Purification and Characterization of Acetate Kinase from Acetate-grown *Methanosarcina thermophila*," 1988 *J. Biol. Chem.* 263:15444-15448.
Alperman, Maria Henriette, "Untersuchungen zum Alternativen Terpenbiosyntheseweg in *Escherichia coli* und *Nicotiana benthamiana*," Doctoral Thesis from the Martin-Luther-Universität Halle-Wittenberg in Wittenberg, Germany. Cover date Jan. 27, 2006. Available online [retrieved on Aug. 11, 2009]. Retrieved from the Internet: < http://sundoc.bibliothek.uni-halle.de/diss-online/06/06H092/prom.pdf>; 154 total pages. English language abstract included.
Aristidou et al., "Modification of Central Metabolic Pathway in *Escherichia coli* to Reduce Acetate Accumulation by Heterologous Expression of the *Bacillus subtilis* Acetolactate Synthase Gene," Oct. 1994 *Biotechnol. Bioeng.* 44:944-951.
Aristidou et al., "Metabolic Engineering of *Escherichia coli* to Enhance Recombinant Protein Production through Acetate Reduction," 1995 *Biotech. Prog.* 11:475-478.
Auzat et al., "The NADH oxidase of *Streptococcus pneumoniae*: its involvement in competence and virulence," 1999 *Mol. Microbiol.* 34(5):1018-1028.
Baba et al., "Construction of *Escherichia coli* K-12 in-frame, single-gene knockout mutants: the Keio collection," 2006 *Mol. Syst. Biol.* 2:1-11.
Babaeipour et al., "A proposed feeding strategy for the overproduction of recombinant proteins in *Escherichia coli*," Feb. 2008 *Biotech. Appl. Biochem.* 49(Pt 2):141-147.
Babul, "Phosphofructokinases from *Escherichia coli*," Jun. 25, 1978 *J. Biol. Chem.* 253(12):4350-4355.

(Continued)

*Primary Examiner* — Christian Fronda
(74) *Attorney, Agent, or Firm* — Mueting, Raasch & Gebhardt, P.A.

(57) ABSTRACT

Microbial production of pyruvate and metabolites derived from pyruvate in cells exhibiting reduced pyruvate dehydrogenase activity compared to wild-type cells. Acetate and glucose are supplied as a carbon sources.

9 Claims, 16 Drawing Sheets

(56) References Cited

OTHER PUBLICATIONS

Brown et al., "The Enzymic Interconversion of Acetate and Acetyl-coenzyme A in Escherichia coli," 1977 J. Gen. Microbiol. 102:327-336.

Bunch et al., "The IdhA gene encoding the fermentative lactate dehydrogenase of Escherichia coli," 1997 Microbiol. 143:187-195.

Causey et al., "Engineering the metabolism of Escherichia coli W3110 for the conversion of sugar to redox-neutral and oxidized products: homoacetate production," Feb. 4, 2003 Proc. Natl. Acad. Sci. USA 100(3):825-832. Available online on Jan. 23, 2003.

Causey et al., "Engineering Escherichia coli for efficient conversion of glucose to pyruvate," Feb. 24, 2004 Proc. Natl. Acad. Sci. USA 101(8):2235-2240. Available online on Feb. 12, 2004.

Chaney et al., "Modified reagents for determination of urea and ammonia," 1962 Clin. Chem 8:130-132.

Chang and Cronan, "Mapping nonselectable genes of Escherichia coli by using transposon Tn10: location of a gene affecting pyruvate oxidase," Sep. 1982 J. Bacteriol. 151(3):1279-1289.

Chang and Cronan, "Genetic and biochemical analyses of Escherichia coli strains having a mutation in the structural gene (poxB) for pyruvate oxidase," May 1983 J. Bacteriol. 154(2):756-762.

Chang et al., "Homofermentative Production of D- or L-Lactate in Metabolically Engineering Escherichia coli RR1," 1999 Appl. Environ. Microbiol. 65(4):1384-1389.

Chao et al., "Alteration of Growth Yield by Overexpression of Phosphoenolpyruvate Carboxylase and Phosphoenolpyruvate Carboxykinase in Escherichia coli," 1993 Appl. Env. Microbiol. 59:4261-4265.

Chatterjee et al., "Mutation of the ptsG gene results in increased production of succinate in fermentation of glucose by Escherichia coli," 2001 Appl Environ Microbiol 67:148-154.

Chen et al., "Observations of Aerobic, Growing Escherichia coli Metabolism Using an On-Line Nuclear Magnetic Resonance Spectroscopy System," 1993 Biotech. Bioeng. 42:215-221.

Cherepanov and Wackernagel, "Gene disruption in Escherichia coli: $Tc^R$ and $Km^R$ cassettes with the option of Flp-catalyzed excision of the antibiotic-resistance determinant," May 26, 1995 Gene 158(1):9-14.

Cicalese et al., "Pyruvate Prevents Ischemia-Reperfusion Mucosal Injury of Rat Small Intestine," 1996 Amer. J. Surg. 171:97-101.

Cicalese et al, "Acute Rejection of Small Bowel Allografts in Rats: Protection Afforded by Pyruvate," 1996 Trans Proc. 28(5):2474.

Clark et al., "Escherichia coli mutants with altered control of alcohol dehydrogenase and nitrate reductase," 1980 J. Bacteriol 141:177-183.

Clark, "The fermentation pathways of Escherichia coli," 1989 FEMS Microbiol. Rev. 63:223-234.

Contiero et al., "Effects of mutations in acetate metabolism on high-cell-density growth of Escherichia coli," 2000 J. Ind. Microbiol. Biotech. 24:421-430.

Cotellessa et al., "The use of pyruvic acid in the treatment of acne," May 2004 J. Eur. Acad. Dermatol. Venereol. 18(3):275-278. Available online on Apr. 15, 2004.

Danson et al., "Intramolecular Coupling of Active Sites in the Pyruvate Dehydrogenase Multienzyme Complex of Escherichia coli," 1978 Biochem J. 175:193-198.

Datsenko and Wanner, "One-step inactivation of chromosomal genes in Escherichia coli K-12 using PCR products," Jun. 6, 2000 Proc. Natl. Acad. Sci. USA 97(12):6640-6645.

Dauner et al., "Bacillus subtilis metabolism and energetics in carbon-limited and excess-carbon chemostat culture," Dec. 2001 J. Bacteriol. 183(24):7308-7317.

Deboer et al., "Pyruvate enhances recovery of rat hearts after ischemia and reperfusion by preventing free radical generation," 1993 Amer. J. Phys. 265: H1571-76.

DeGraef et al., "The steady-state internal redox state (NADH/NAD) reflects the external redox state and is correlated with catabolic adaptation in Escherichia coli," 1999 J. Bacteriol 181:2351-2357.

de Kok, et al., "The pyruvate dehydrogenase multi-enzyme complex from Gram-negative bacteria," 1998 Biochimica et Biophysica Acta 1385:353-366.

Diaz-Ricci et al., "Effect of Alteration of the Acetic Acid Synthesis Pathway on the Fermentation Pattern of Escherichia coli," 1991 Biotech. Bioeng. 38:1318-1324.

Dickely et al., "Isolation of Lactococcus lactis nonsense suppressors and construction of a food-grade cloning vector," 1995 Molecular Microbiology 15(5):839-847.

Eiteman et al., "Optimization of the ion-exchange analysis of organic acids from fermentation," 1997 Anal. Chim. Acta. 338:69-75.

Eiteman and Altman, "Engineering Escherichia coli for the production of C3 biochemicals pyruvate and alanine," Grant Abstract, Project No. GEO-2003-01116 / Grant No. 2003-35504-13666 [online]. USDA CSREES Non-Food Characterization/Process/Product Program, project dates Sep. 1, 2003, to Aug. 31, 2007 [retrieved on Oct. 8, 2010]. Retrieved from the Internet: <http://cris.csrees.usda.gov//cgi-bin/starfinder/25669/crisassist.txt?action=k2yiNkJP__stfw4>; 6 pgs.

El-Mansi et al., "Control of Carbon Flux to Acetate Excretion During Growth of Escherichia coli in Batch and Continuous Cultures," 1989 J. Gen. Microbiol. 135:2875-2883.

Farmer et al., "Reduction of Aerobic Acetate Production by Escherichia coli," 1997 Appl. Environ. Microbiol. 63:3205-3210.

Flores et al., "Expression of PEP carboxylase from Escherichia coli complements the phenotypic effects of pyruvate carboxylase mutations in Saccharomyces cerevisiae," Aug. 4, 1997 FEBS Letters 412(3):531-534.

Futai et al., "Inducible membrane-bound L-lactate dehydrogenase from Escherichia coli," Aug. 25, 1977 J. Biol. Chem. 252:5820-5827.

Galkin et al., "Synthesis of Optically Active Amino Acids from α-Keto Acids with Escherichia coli Cells Expressing Heterologous Genes," 1997 Appl. Environ. Microbiol. 63(12):4651-4656.

Garrett and Grisham, Biochemistry; $2^{nd\ Edition}$. Harcourt Brace College Publishers: Fort Worth, TX; Copyright 1999. Cover page, publisher's page, and table of contents (21 pgs).

Georgellis et al., "Quinones as the redox signal for the arc two-component system of bacteria," Jun. 22, 2001 Science 292(5525):2314-2316.

Georgiou et al., "Identification of the cydC locus required for expression of the functional form of the cytochrome d terminal oxidase complex in Escherichia coli," May 1987 J. Bacteriol. 169(5):2107-2112.

Gerharz et al., "Produktion von Pyruvat aus Glucose mit Escherichia coli," Biokatalyse, Heidelberg, Germany, 2001, pp. 29-33. Provided with English-language translation.

Gerharz, Tanja, "Pyruvat-Production durch acetatauxotrophe Escherichia coli—Stämme," Doctoral Dissertation from Heinrich-Heine-Universität, Düsseldorf, Germany; Cover date Jul. 2003; oral defense date May 28, 2003. 142 Pages.

Gerharz, Tanya, "Pyruvat-Produktion durch acetatauxotrophe Escherichia coli—Stämme," Doctoral Dissertation from Heinrich-Heine-Universität; Düsseldorf, Germany; Cover date Jul. 2003, oral defense date May 28, 2003. Abstract with English language translation available online from Dublin Core Metadata Initiative database [retrieved on Oct. 20, 2011]. Retrieved from the Internet: <http://deposit.d-nb.de/cgi-binlfrontmetaviewer.pl?idn=969699182>; 4 pages.

Gokarn et al., "Metabolic Analysis of Escherichia coli in the Presence and Absence of the Carboxylating Enzymes Phosphoenolpyruvate Carboxylase and Pyruvate Carboxylase," 2000 Appl. Environ. Microbiol. 66(5):1844-1850.

Gottschalk, "Bacterial Metabolism", Second Edition. 1979, 1986 by Springer-Verlag, New York Inc., Title Page, Copyright Page and Table of Contents Only.

Grabau et al., "Nucleotide sequence and deduced amino acid sequence of Escherichia coli pyruvate oxidase, a lipid-activated flavoprotein," 1986 Nucleic Acids Res. 14(13):5449-60.

Grimshaw et al.,"Kinetic mechanism of Bacillus subtilis L-alanine dehydrogenase," Sep. 29, 1981 Biochemistry 20:5650-5655.

(56) References Cited

OTHER PUBLICATIONS

Guest, "Anaerobic Growth of *Escherichia coli* K12 with Fumarate as Terminal Electron Acceptor, Genetic Studies with Menaquinone and Fluoroacetate-resistant Mutants," 1979 *J. Gen. Microbiol.* 115:259-271.

Guyer et al., "Identification of a Sex-factor-affinity Site in *E. coli* as γδ," 1981 *Cold Spring Harbor Symp. Quant. Biol.* 45:135-140.

Harary et al., "Biosynthesis of dicarboxylic acids by carbon dioxide fixation. VII. Equilibrium of 'malic' enzyme reaction," 1953 *J. Biol. Chem.* 203:595-604.

Hashimoto et al., "L-Alanine fermentation by an alanine racemase-deficient mutant of the DL-alanine hyperproducing bacterium *Arthrobacter oxydans* HAP-1," 1998 *J. Ferment. Bioeng.* 86(4):385-390.

Hashimoto and Katsumata, "Mechanism of alanine hyperproduction by *Arthrobacter oxydans* HAP-1: metabolic shift to fermentation under nongrowth aerobic conditions," Jun. 1999 *Appl. Environ. Microbiol.* 65(6):2781-2783.

Hein et al., "Biochemical and Molecular Characterization of the *Alcaligenes eutrophus* Pyruvate Dehydrogenase Complex and Identification of a New Type of Dihydrolipoamide Dehydrogenase," Jul. 1994 *J. Bacteriol.* 176(14):4394-4408.

Hein et al., "*Alcaligenes eutrophus* possesses a second pyruvate dehydrogenase (E1)," May 1, 1996 *Eur. J. Biochem.* 237(3):674-84.

Henriksen et al., "Redirection of pyruvate catabolism in *Lactococcus lactis* by selection of mutants with additional growth requirements," 2001 *Appl. Microbial Biotechnol.* 56:767-775.

Herbert et al., "Biochemical and Genetic Studies with Lysine + Methionine Mutants of *Escherichia coli*: Lipoic Acid and α-Ketoglutarate Dehydrogenase-less Mutants," 1968 *J. Gen. Microbiol.* 53:363-381.

Holmström et al., "Improved tolerance to salinity and low temperature in transgenic tobacco producing glycine betaine," Feb. 2000 *J. Exp. Bot.* 51(343):177-185.

Holtzclaw et al., "Degradative Acetolactate Synthase of *Bacillus subtilis*: Purification and Properties," 1975 *J. Bacteriol.* 121:917-922.

Horn et al., "High volumetric yields of functional dimeric miniantibodies in *Escherichia coli*, using an optimized expression vector and high-cell-density fermentation under non-limited growth conditions," 1996 *Appl. Microbiol. Biotech.* 46:524-534.

Ingram et al., "Expression of different levels of Ethanologenic enzymes from *Zymomonas mobilis* in Recombinant Strains of *Escherichia coli*," 1988 *Appl. Environ. Microbiol.* 54:397-404.

International Search Report issued in PCT/US03/05083, dated Sep. 9, 2004.

International Preliminary Examination Report issued in PCT/US03/05083, dated May 2, 2007.

Iuchi et al., "Effects of nitrate respiration on expression of the Arc-controlled operons encoding succinate dehydrogenase and flavin-linked L-acetate dehydrogenase," Mar. 1994 *J. Bacteriol.* 176(6):1695-1701.

Ivy et al., "Effects of pyruvate on the metabolism and insulin resistance of obese Zucker rats," 1994 *Amer. J. Clin. Nutr.* 59:331-37.

Izumi et al., "Pyruvic Acid Production from 1,2-Propanediol by Thiamin-requiring *Acinetobacter* sp. 80-M," 1982 *Agr. Biol. Chem.* 46:2673-2679.

Jensen et al., "Production of Recombinant Human growth Hormone in *Escherichia coli*: Expression of Different Precursors and Physiological effects of Glucose, Acetate, and Salts," 1990 *Biotech. Bioeng.* 36:1-11.

Kessler et al., "Anaerobic dissimilation of pyruvate," in *Escherichia coli and Salmonella*. Neidhardt et al. (eds). ASM Press: Washington, D.C. 1996; cover page, publisher's page and pp. 199-205.

Kitajima-Ihara et al., "Rotenone-insensitive internal NADH-quinone oxidoreductase of *Saccharomyces cerevisiae* mitochondria: the enzyme expressed in *Escherichia coli* acts as a member of the respiratory chain in the host cells," Jan. 2, 1998 *FEBS Letters* 421(1):37-40.

Knappe et al., "A radical-chemical route to acetyl CoA—the anaerobically induced pyruvate formate-lyase system of *Escherichia coli*," 1990 *FEMS Microbiol. Rev.* 75:383-398.

Koebmann et al., "The glycolytic flux in *Escherichia coli* is controlled by the demand for ATP," Jul. 2002 *J. Bacteriol.* 184(14):3909-3916.

Kotlarz et al., "Regulation of the amount and of the activity of phosphofructokinases and pyruvate kinases in *Escherichia coli*," Feb. 13, 1975 *Biochim. Biophys. Acta.* 381(2):257-268.

Kuroda et al., "Alanine dehydrogenase from two *Bacillus* species with distinct thermostabilities: molecular cloning, DNA and protein sequence determination, and structural comparison with other NAD(P)+-dependent dehydrogenases," 1990 *Biochemistry* 29:1009-1015.

Lamed et al., "Thermostable, Ammonium-Activated Malic Enzyme of *Clostridium thermocellum*," 1981 *Biochim. et Biophys. Acta.* 660:251-255.

Lawson et al., "Disruption and Mutagenesis of the *Saccharomyces cerevisiae* PDX1 Gene Encoding the Protein X Component of the Pyruvate Dehydrogenase Complex," 1991 *Biochemistry* 30:2834-2839.

Lee et al., "Control of fed-batch fermentations," Apr. 1999 *Biotechnol. Adv.* 17(1):29-48.

Lee et al., "Aerobic production of alanine by *Escherichia coli* aceF ldhA mutants expressing the *Bacillus sphaericus* alaD gene," 2004 *Appl. Microbiol. Biotechnology* 65:56-60.

Lessard et al., "Expression in *Escherichia coli* of Genes Encoding the E1 α and Eβ Subunits of the Pyruvate Dehydrogenase Complex of *Bacillus stearothermophilus* and Assembly of a Functional E1 Component ($\alpha_2\beta_2$) in Vitro," 1994 *J. Bio. Chem.* 269(14):10378-10383.

LeVine et al., "Isolation and Characterization of Acetate Kinase and Phosphotransacetylase Mutants of *Escherichia coli* and *Salmonella Typhimurium*," 1980 *J. Bact.* 143:1081-1085.

Li et al., "Biotechnological Production of Pyruvic Acid," 2001 *Appl. Microbiol. Biotechnol.* 57(4):451-459.

Loewen et al., "Regulation in the rpoS regulon of *Escherichia coli*," 1998 *Can. J. Microbiol.* 44:707-717.

Lopez de Felipe et al., "Cofactor Engineering: a Novel Approach to Metabolic Engineering in *Lactococcus lactis* by Controlled Expression of NADH Oxidase," 1998 *J. Bacter.* 180:3804-3808.

Lopez de Felipe et al., "The role of NADH-oxidation in acetoin and diacetyl production from glucose in *Lactococcus lactis* subsp. *Lactis* MG1363," 1997 *FEMS Microbiol. Lett.* 156:15-19.

Luli et al., "Comparison of Growth, Acetate Production, and Acetate Inhibition of *Escherichia coli* Strains in Batch and Fed-Batch Fermentations," 1990 *Appl. Environ. Micro.* 56:1004-1011.

MacLean et al., "The role of glyoxalase I in the detoxification of methylglyoxal and in the activiation of the KefB K+ efflux system in *Escherichia coli*," Feb. 1998 *Mol. Microbiol.* 27(3):563-571.

Maloy et al., "Elevated levels of glyoxylate shunt enzymes in *Escherichia coli* strain constitutive for fatty acid degradation," 1980 *J. Bacteriol.* 143:720-725.

Mat-Jan et al., "Mutants of *Escherichia coli* Deficient in the Fermentative Lactate Dehydrogenase," 1989 *J. Bacter.* 171:342-348.

Miyata et al., "Breeding of High-Pyruvate-Producing *Torulopsis glabrata* with Acquired Reduced Pyruvate Decarboxylase," 1999 *J. Biosci. Bioeng.* 88:173-177.

Miyata et al , "Improvement of Fermentative Production of Pyruvate from Glucose by *Torulopsis glabrata* IFO 0005," 1996 *J. Ferm. Bioeng.* 82:475-479.

Moriguchi, "Fermentative Production of Pyruvic Acid from Citrus Peel Extract by *Debaryomyces coudertii*," 1982 *Agr. Biol. Chem.* 46:955-961.

Murooka et al., eds. "Recombinant Microbes for Industrial and Agricultural Applications," in *Bioprocess Technology Series*, vol. 19. Marcel Dekker, Inc.: New York, N.Y; 1994. Title Page, Copyright Page and Table of Contents only.

Nakano et al., "Characterization of Anaerobic Fermentative Growth of *Bacillus subtilis*: Identification of Fermentation End Products and Genes Required for Growth," Nov. 1997 *J. Bacteriology.* 179(21):6749-6755.

Nakazawa et al., "Synthesis of L-Tryptophan from Pyruvate, Ammonia and Indole," 1972 *Agr. Biol. Chem.* 36:2523-2528.

(56) References Cited

OTHER PUBLICATIONS

Nemeria et al, "Inhibition of the *Escherichia coli* Pyruvate Dehydrogenase Complex E1 Subunit and Its Tyrosine 177 Variants by Thiamin 2-Thiazolone and Thiamin 2-Thiothiazolone Diphosphates," 2001 *J. Biol. Chem.* 276(49):45969-45978.

O'Beirne et al., "The utilisation of glucose/acetate mixtures by *Escherichia coli* W3110 under aerobic growth conditions," 2000 *Bioprocess Eng.* 23:375-380.

Ohashima et al., "Purification and Properties of Alanine Dehydrogenase from *Bacillus sphaericus*," 1979 *Eur. J. Biochem.* 100:29-39.

Office Action from the European Patent Office in EP Pat. Appl. No. 03 713 556.3: EPO Form 2001 (1 page) and EPO Form 2906 (3 pages), Jan. 9, 2009.

Office Action from the European Patent Office in EP Pat. Appl. No. 03 713 556.3: EPO Form 2001 (2 pages) and EPO Form 2906 (3 pages), Dec. 15, 2010.

Oliver, "Demand management in cells," Jul. 4, 2002 *Nature* 418:33-34.

Ono et al., "ATP synthase that lacks $F_0\alpha$-subunit: isolation properties, and indication of $F_0\beta_2$-subunits as an anchor rail of a rotating $c$-ring," Aug. 6, 2004 *J. Biol. Chem.* 279(32):33409-33412. Available online on Jun. 2, 2004.

Oshima et al., "Thermostable alanine dehydrogenase from thermophilic *Bacillus sphaericus* DSM 462," 1990 *Eur. J Biochem.* 191:715-720.

Park, Sung Min, "Investigation of carbon fluxes in central metabolic pathways of *Corynebacterium glutamicum*," Doctoral Dissertation; Department of Chemical Engineering at Massachusetts Institute of Technology. Jun. 1996. 274 pages.

Peters-Wendisch, Petra, "Anaplerotic reactions in Corynebacterium glutamicum: Investigations of the importance of PEP carboxylase and pyruvate carboxylase in the central metabolism and in amino acid production," Doctoral Dissertation; Institute for Biotechnology at University of Dusseldorf. Aug. 1996. English language translation included. 279 pages.

Peters-Wendisch et al., "Pyruvate carboxylase from *Corynebacterium glutamicum*: characterization, expression and inactivation of the pyc gene," 1998 *Microbiol.* 144:915-927.

Peters-Wendisch et al., "Pyruvate Carboxylase is a Major Bottleneck for Glutamate and Lysine Production by *Corynebacterium glutamicum*," 2001 *J. Mol. Microbiol. Biotechnol.* 3:295-300.

Quail et al., "The *pdhR-aceEF-lpd* operon of *Escherichia coli* expresses the pyruvate dehydrogenase complex," 1994 *Molecular Microbiology* 12(1):95-104.

Ra et al., "Effects of gene disruptions in the nisin gene cluster of *Lactococcus lactis* on nisin production and producer immunity," 1999 *Microbiology* 145:1227-1233.

Rae et al., "Sequences and Expression of Pyruvate Dehydrogenase Genes from *Pseudomonas aeruginosa*," Jun. 1997 *J. Bacteriology* 179(11):3561-3571.

Ross et al., "Molecular cloning and analysis of the gene encoding the NADH oxidase from *Streptococcus faecalis* 10C1" Oct. 5, 1992 *J. Mol. Bio.* 227(3):658-671.

Roufs, "Pyruvate: does it amp endurance and burn more fat?," Dec. 1996 *Muscle and Fitness* pp. 87, 88, 195, and 197.

Russell et al., "Overproduction of the pyruvate dehydrogenase multienzyme complex of *Escherichia coli* and site-directed substitutions in the E1p and E2p subunits," Oct. 15, 1992 *Biochem. J.* 287(Pt 2):611-619.

Ruyter et al., "Control of glucose metabolism by enzyme $II^{Glc}$ of the phosphoenolpyruvate-dependent phosphotransferase system in *Escherichia coli*," Oct. 1991 *J. Bacteriol.* 173(19):6184-6191.

Saadat and Harrison, "Identification of catalytic bases in the active site of *Escherichia coli* methylglyoxal synthase: cloning, expression, and functional characterization of conserved aspartic acid residues," Jul. 14, 1998 *Biochem.* 37:10074-10086.

Schaaff et al., "Overproduction of glycolytic enzymes in yeast," Jul.-Aug. 1989 *Yeast* 5(4):285-290.

Schulze et al., "Time-resolved fluorescence studies on mutants of the dihydrolipoyl transacetylase (E2) component of the pyruvate dehydrogenase complex from *Azotobacter vinelandii*," Oct. 1990 *FEBS Lett.* 273(1/2):46-50.

Schulze et al., "Site-directed mutagenesis of the dihydrolipoyl transacetylase component (E2p) of the pyruvate dehydrogenase complex from *Azotobacter vinelandii*," 1991 *Eur. J. Biochem.* 202:841-848.

Siranosian et al., "Alanine dehydrogenase (*ald*) is required for normal sporulation in *Bacillus subtilis*," 1993 *J. Bacteriol.* 175:6789-6796.

Smith et al., "Fed-batch two-phase production of alanine by a metabolically engineered *Escherichia coli*," Oct. 2006 *Biotech. Lett.* 28(20):1695-1700.

Snoep et al., "Isolation and characterisation of the pyruvate dehydrogenase complex of anaerobically grown *Enterococcus faecalis* NCTC 775," 1992 *Eur. J. Biochem.* 203:245-250.

Snoep et al., "Isolation, Characterization, and Physiological Role of the Pyruvate Dehydrogenase Complex and $\alpha$-Acetolactate Synthase of *Lactococcus lactis* subsp. *lactis* bv. diacetylactis," Jul. 1992 *J. Bacteriology* 174(14):4838-4841.

Sorgen et al., "Deletions in the second stalk of $F_1F_0$-ATP synthase in *Escherichia coli*," Oct. 23, 1998 *J. Biol. Chem.* 273(43):27873-27878.

Soto et al., "The Disruption of a Gene Encoding a Putative Arylesterase Impairs Pyruvate Dehydrogenase Complex Activity and Nitrogen Fixation in *Sinorhizobium meliloti*," 2001 *MPMI* 14(6):811-815.

Stanko et al., "Pyruvate Inhibits Growth of Mammary Adenocarcinoma 13762 in Rats," 1994 *Can. Res.* 54:1004-1007.

Stanko et al., "Pyruvate supplementation of a low-cholesterol, low-fat diet: effects on plasma lipid concentrations and body composition in hyperlipidemic patients," Feb. 1994 *Amer. J. Clin. Nutr.* 59(2):423-427.

Stanko et al., "Body composition, energy utilization, and nitrogen metabolism with a 4.25-MJ/d low-energy diet supplemented with pyruvate," 1992 *Am. J. Clin. Nutr.* 56:630-635.

Stanko et al., "Body composition, energy utilization and nitrogen metabolism with a severely restricted diet supplemented with dihydroxyacetone and pyruvate," 1992 *Am. J. Clin. Nutr.* 55:771-776.

Stanko et al., "Enhanced leg exercise endurance with a high-carbohydrate diet and dihydroxyacetone and pyruvate," 1990 *J. Appl. Phys.* 69(5):1651-56.

Stanko et al., "Enhancement of arm exercise endurance capacity with dihydroxyacetone and pyruvate," 1990 *J. Appl. Phys.* 68(1):119-24.

Stephanopoulos, et al., "Metabolic Fluxes and Metabolic Engineering," 1999 *Metabolic Engineering*1,1-11. Article No. MT980101.

Stryer, *Biochemistry*, Third Edition. W.H. Freeman and Company, New York. 1988 by Lubert Stryer (Stanford University). Title Page, Copyright Page and Table of Contents Only.

Taguchi et al., "D-Lactate Dehydrogenase Is a Member of the D-Isomer-specific 2-Hydroxyacid Dehydrogenase Family," 1991 *J. Biol. Chem.* 266:12588-12594.

Takao et al., "Pyruvic Acid Production by *Schizophyllum commune*," 1982 *J. Ferm. Tech.* 60: 277-280.

Takors et al., "Pyruvat-Produktion aus Glucose mit rekombinanten *Escherichia coli*-Stämmen," *Transkript*, Sonderband Nachhaltige Biokatalyse, 2003, 96-99. Provided with English-language translation.

Terada et al., "Site-Directed Mutagenesis of Phosphoenolpyruvate Carboxylase from *E. coli*: The Role of His[579] in the Catalytic and Regulatory Functions," 1991 *J. Biochem.* 109:49-54.

Tomar et al., "Production of Pyruvate by *Escherichia coli*." Poster, presented at the *Society for Industrial Microbiology (SIM) Annual Meeting*, on Aug. 13, 2002, Philadelphia, PA. Poster abstract available Aug. 11, 2002.

Tomar et al., "The Effect of Acetate Pathway Mutations on the Production of Pyruvate in *Escherichia coli*," Jul. 2003 *Appl. Microbiol. Biotechnol.* 62(1):76-82. Available online Feb. 26, 2003.

Tomar, A. "Production of Pyruvate by *Escherichia coli* Using Metabolic Engineering," Dissertation. University of Georgia Electronic Theses and Dissertations. (Aug. 11, 2003).

(56) References Cited

OTHER PUBLICATIONS

Tosaka et al., "The role of biotin-dependent pyruvate carboxylase in L-lysine production," 1979 *Agric. Biol. Chem.* 43:1513-1519.
Uhlenbusch et al., "Expression of an L-alanine dehydrogenase gene in *Zymomonas mobilis* and excretion of L-alanine," 1991 *Appl. Environ. Microbiol.* 57:1360-1366.
Ui, "Purification and Properties of NADPH-linked Diacetyl Reductase (S-Acetoin Forming) from *Bacillus polymyxa*," 1987 *Agr. Biolog. Chem.* 51:1447-1448.
Underwood et al., "Lack of protective osmolytes limits final cell density and volumetric productivity of ethanologenic *Escherichia coli* KO11 during xylose fermentation," May 2004 *Appl. Environ. Microbiol.* 70:2734-2740.
VanBogelen et al., "Global analysis of proteins synthesized during phosphorus restriction in *Escherichia coli*," Aug. 1996 *J. Bacteriol.* 178(15):4344-4366.
Vemuri et al., "Succinate production in dual-phase *Escherichia coli* fermentations depends on the time of transition from aerobic to anaerobic conditions," Jun. 2002 *J. Ind. Microbiol. Biotech.* 28:325-332.
Vemuri et al., "Effects of Growth Mode and Pyruvate Carboxylase on Succinic Acid Production by Metabolically Engineered Strains of *Escherichia coli*," Apr. 2002 *Applied and Environmental Microbiology*, vol. 68 (4):1715-1727.
Vemuri et al., "Overflow metabolism in *Escherichia coli* during steady-state growth: transcriptional regulation and effect of the redox ratio," May 2006 *Appl. Environ. Microbiol.* 72:3653-3661.
Wimpenny and Firth, "Levels of nicotinamide adenine dinucleotide and reduced nicotinamide adenine dinucleotide in facultative bacteria and the effect of oxygen," Jul. 1972 *J. Bacteriol.* 111:24-32.
Wise, "The measurement of the aeration of culture media," 1951 *J. Gen. Microbiol.* 5:167-177.
Xu et al., "Biotechnological routes to pyruvate production," Mar. 2008 *J. Biosci. Bioeng.* 105(3):169-175.
Yamada et al., "Synthesis of *L*-Tyrosine from Pyruvate, Ammonia and Phenol by Crystalline Tyrosine Phenol Lyase," 1972 *Biochem. Biophys. Res. Comm.* 46:370-374.
Yancey, "Organic osmolytes as compatible, metabolic and counteracting cytoprotectants in high osmolarity and other stresses," Aug. 2005 *J. Exp. Biol.* 208:2819-2830.
Yazdani and Gonzalez, "Anaerobic fermentation of glycerol: a path to economic viability for the biofuels industry," Jun. 2007 *Curr. Opin. Biotechnol.* 18:213-217. Available online on May 25, 2007.
Yokota et al., "Conversion of Pyruvic Acid Fermentation to Tryptophan Production by the Combination of Pyruvic Acid-producing Microorganisms and *Enterobacter aerogenes* Having High Tryptophanase Activity," 1984 *Agr. Biol. Chem.* 48:2663-2668.
Yokota et al., "Pyruvic Acid Production by Lipoic Acid Auxotrophs of *Enterobacter aerogenes*," 1989 *Agr. Biol. Chem.* 53:705-711.
Yokota et al., "Pyruvic Acid Production by an F1-ATPase-defective Mutant of *Escherichia coli* W1485lip2," 1994. *Biosci. Biotech. Biochem.* 58(12):2164-2167.
Yokota et al., "Pyruvic acid production by a lipoic acid auxotroph of *Escherichia coli W1485*," 1994 *Appl. Microbiol. Biotech.* 41:638-643.
Yonehara et al., "Fermentative Production of Pyruvate from Glucose by *Torulopsis glabrata*," 1994 *J. Ferm. Bioeng.* 78:155-159.
Yu et al., "An efficient recombination system for chromosome engineering in *Escherichia coli*," May 23, 2000 *Proc. Natl. Acad. Sci. USA* 97(11):5978-5983.

Yu et al., "Characterization of the *Streptococcus pneumoniae* NADH oxidase that is required for infection," Feb. 2001 *Microbiology* 147(Pt 2):431-438.
Zeeman et al., "Inactivation of the *Kluyveromyces lactis K1PDA1* gene leads to loss of pyruvate dehydrogenase activity, impairs growth on glucose and triggers aerobic alcoholic fermentation," 1998 *Microbiology* 144:3437-3446.
Zelic et al., "Process development for *Escherichia coli* based pyruvate production," Poster abstract from *biocat 2002 Book of Abstracts*; p. 194. Hamburg, Germany; Jul. 28-31, 2002. Available online [retrieved on Oct. 8, 2010]. Retrieved from the Internet: <http://crosbi.znanstvenici.hr/prikazi-rad?rad=108346 &table=zbornik&lang=EN&print=true>; 2 pages.
Zelic et al., "Fed-batch process for pyruvate production by recombinant *Escherichia coli* YYC202 strain," Jul. 2003 *Eng. Life Sci.*, 3(7):299-305. Available online on Jul. 7, 2003.
Zelić, Bruno, "Study of the Process Development for *Escherichia coli* Based Pyruvate Production," Doctoral Dissertation; Faculty of Chemical Engineering and Technology at University of Zagreb, Croatia. Cover date Jul. 2003. 136 pages.
Zelic et al., "Process Strategies to Enhance Pyruvate Production With Recombinant *Escherichia coli*: From Repetitive Fed-Batch to In Situ Product Recovery With Fully Integrated Electrodialysis," Mar. 20, 2004 *Biotechnology and Bioengineering* 85(6): 638-646. Available online on Jan. 20, 2004.
Zelic et al., "Modeling of the pyruvate production with *Escherichia coli* in a fed-batch bioreactor," Jul. 2004 *Bioprocess Biosyst. Eng.* 26(4): 249-258. Available online on Apr. 15, 2004.
Zhou et al., "Betaine tripled the volumetric productivity of D(-)-lactate by *Escherichia coli* strain SZ132 in mineral salts medium," May 2006 *Biotech. Lett.* 28:671-676.
Zhu et al., "Homolactate fermentation by metabolically engineered *Escherichia coli* strains," Jan. 2007 *Appl. Environ. Microbiol.* 73(2):456-464. Available online on Nov. 22, 2006.
Zhu et al., "Indirect monitoring of acetate exhaustion and cell recycle improve lactate production by non-growing *Escherichia coli*," 2008 *Biotechnol. Lett.* 30:1943-1946. Available online on Jun. 25, 2008.
Zhu, Yihui, "Production of pyruvate and lactate by metabolically engineering *Escherichia coli*," Ph.D. thesis from the Department of Biological and Agricultural Engineering at the University of Georgia. Cover date Aug. 2008; available in the University of Georgia dissertations database on Apr. 6, 2009. Available online [retrieved on Jul. 12, 2010]. Retrieved from the Internet: < http://dbs.galib.uga.edu/cgi-bin/ultimate.cgi?dbs=getd&userid=galileo&serverno=8 &instcode=publ&_cc=1>; 141 pages.
Zhu et al., "High glycolytic flux improves pyruvate production by a metabolically engineered *Escherichia coli* strain," Nov. 2008 *Appl. Environ. Microbiol.* 74(21):6649-6655. Available online on Sep. 19, 2008.
Zhu et al., "Conversion of glycerol to pyruvate by *Escherichia coli* using acetate- and acetate/glucose-limited fed-batch processes," Mar. 2010 *J. Indust. Microbiol. Biotechnol.* 37(3):307-312. Available online on Dec. 13, 2009.
Zubay, Geoffrey (Columbia University), *Biochemistry, Third Edition*. Wm. C. Brown Publishers: Dubuque, IA; 1993. Title Page, Copyright Page and Table of Contents Only.
Office Action issued in U.S. Appl. No. 10/923,458, on Jun. 12, 2008.
Office Action issued in U.S. Appl. No. 10/923,458, on Jan. 27, 2009.
Office Action issued in U.S. Appl. No. 10/923,458, on Jul. 21, 2009.
Office Action issued in U.S. Appl. No. 12/825,059, on Nov. 22, 2011.

* cited by examiner

```
                        SEQUENCE LISTING

<160> NUMBER OF SEQ ID NOS: 4

<210> SEQ ID NO 1
<211> LENGTH: 70
<212> TYPE: DNA
<213> ORGANISM: artificial
<220> FEATURE:
<223> OTHER INFORMATION: synthetic oligonucleotide primer

<400> SEQUENCE: 1
atgtacatta tggaactgac gactcgcact ttacctgcgc ggaaacatat ttgagaagca      60
cacggtcaca                                                            70

<210> SEQ ID NO 2
<211> LENGTH: 70
<212> TYPE: DNA
<213> ORGANISM: artificial
<220> FEATURE:
<223> OTHER INFORMATION: synthetic oligonucleotide primer

<400> SEQUENCE: 2
ttacttcaga cggtccgcga gataacgctg ataatcgggg atcagaatat tacctgtgac      60
ggaagatcac                                                            70

<210> SEQ ID NO 3
<211> LENGTH: 20
<212> TYPE: DNA
<213> ORGANISM: artificial
<220> FEATURE:
<223> OTHER INFORMATION: synthetic oligonucleotide primer

<400> SEQUENCE: 3
ggaactgacg actcgcactt                                                 20

<210> SEQ ID NO 4
<211> LENGTH: 20
<212> TYPE: DNA
<213> ORGANISM: artificial
<220> FEATURE:
```

```
<223> OTHER INFORMATION: synthetic oligonucleotide primer

<400> SEQUENCE: 4
ttacttcaga cggtccgcga                                              20
```

MICROBIAL PRODUCTION OF PYRUVATE AND OTHER METABOLITES

This application is a continuation application of U.S. patent application Ser. No. 12/825,059, which claims the benefit of U.S. Provisional Application No. 61/274,252, filed Aug. 14, 2009, and which is a continuation-in-part application of U.S. patent application Ser. No. 10/923,458, filed Aug. 20, 2004, which is a continuation-in-part of International Application No. PCT/US03/05083, filed Feb. 20, 2003, which claims the benefit of U.S. Provisional Application No. 60/359,279, filed Feb. 20, 2002, and U.S. Provisional Application No. 60/402,747, filed Aug. 12, 2002, all of which are incorporated by reference in their entireties.

BACKGROUND OF THE INVENTION

In stating a vision for the future in "Biobased Industrial Products, Priorities for Research and Commercialization", the National Research Council has proposed U.S. leadership for the global transition to biobased products. The report provides compelling evidence for a competitively priced biobased products industry that will eventually replace much of the petrochemical industry. In light of this report and the desirability of reducing U.S. reliance on foreign oil, there is an increasing interest in generating commodity and fine chemicals from widely available U.S. renewable resources, e.g., crops, through fermentation. In the last few years, companies have invested hundreds of millions of dollars in commercializing the microbial production of several biochemicals, such as lactic acid.

Microbial fermentation processes are used to generate a wide variety of important biochemicals such as ethanol and lysine (markets in the billions of U.S. dollars). In order to be economic, fermentations rely on microorganisms which have been developed by selection or genetic means to accumulate a specific product that is produced via metabolism. Microbial metabolic pathways are not naturally optimal for the generation of a desired chemical, but have instead evolved for the benefit of the organism. Metabolic engineering is the targeted and rational alteration of metabolism, and it involves the redirection of cellular activities to generate a new product or generate a product at a higher rate or yield.

Pyruvate (pyruvic acid) is a three-carbon ketoacid synthesized at the end of glycolysis. Pyruvate is an important raw material for the production of L-tryptophan, L-tyrosine, 3,4-dihydroxyphenyl-L-alanine, and for the synthesis of many drugs and biochemicals. Pyruvate has use in the chemical industry and finds wide application in cosmetics. Clinical studies have found that pyruvate can promote weight loss and fat loss, hence it is commonly marketed in tablet form as a dietary supplement. Recent research indicates that pyruvate also functions as an antioxidant, inhibiting the production of harmful free radicals.

Certain microorganisms have been found to produce useful quantities of pyruvate from glucose, an inexpensive substrate derived from corn starch. The yeasts *Debaryomyces coudertii* (M. Moriguchi, *Agr. Biol. Chem.* 46: 955-961 (1982)) and *Saccharomyces exiguus* (A. Yokota et al., *Agr. Biol. Chem.* 48: 2663-2668 (1984)), for example, are known to accumulate pyruvate, as are the basidiomycetes *Schizophyllum commune* (S. Takao et al., *J. Ferm. Tech.* 60: 277-280 (1982)), and *Agricus campestris* (A. Yokota et al., *Agr. Biol. Chem.* 48: 2663-2668 (1984)). The yeast strain *Torulopsis glabrata* IFO 0005 was found to be a superior strain for the production of pyruvate (T. Yonehara et al., *J. Ferm. Bioeng.* 78: 155-159 (1994)), accumulating 67.8 g/L pyruvate in 63 hours (yield 0.494) in a fed-batch fermentation with successive additions of glucose (R. Miyata et al., *J. Ferm. Bioeng.* 82: 475-479 (1996)). A higher yield (0.673) of pyruvate was observed in *T. glabrata* ACII-33, a mutant with decreased pyruvate decarboxylase (PDC) activity (R. Miyata et al., *J. Biosci. Bioeng.* 88: 173-177 (1999)). Decreased PDC activity prevented the formation of acetate via acetaldehyde and thus increased the pyruvate production. *T. glabrata* ACII-33 accumulated 60.3 g/L pyruvate in 47 hours in a 3 L jar fermenter.

Bacteria of the genera *Corynebacterium* (A. Yokota et al., *Agr. Biol. Chem.* 48: 2663-2668 (1984)) and *Acinetobacter* (Y. Izumi et al., *Agr. Biol. Chem.* 46: 2673-2679 (1982)), *Enterobacter aerogenes* (A. Yokota et al., *Agr. Biol. Chem.* 48: 705-711 (1989)), and *Escherichia coli* (A. Yokota et al., *Appl. Microbiol. Biotech.* 41: 638-643 (1994)) are also known to accumulate pyruvate. A lipoic acid auxotroph of *E. coli* (strain W1485lip2) was found to produce pyruvate aerobically from glucose under lipoic acid deficient conditions. This strain accumulated 25.5 g/L pyruvate in 32 hours with a yield of 0.51 in polypepton (4 g/L) supplemented media (A. Yokota et al., *Appl. Microbiol. Biotech.* 41: 638-643 (1994)).

Alanine, which is derived from pyruvate, is an alpha amino acid that is also commercially important, for example as a starting material in the chemical industry. L-alanine is a chiral building block being one of the smallest chiral compounds, with four important functional groups: hydrogen, methyl, amino, and carboxylic acid. Presently, alanine is produced using metabolically engineered *Corynebacterium* or *Brevibacterium* bacterial strains in which alanine dehydrogenase is overexpressed. However, the efficiency of this method of production is limited because large quantities of carbon move from pyruvate to acetyl-CoA and therefore are unavailable for alanine production.

Diacetyl, also derived from pyruvate, is a flavoring/texture agent for dairy products, and could find additional use in food products.

These compounds (pyruvate, alanine and diacetyl) have current market prices from $10 to $50/pound. Improved production methods from renewable resources would open new markets for pyruvate and its derivatives and thus reduce reliance on petroleum-derived products.

SUMMARY OF THE INVENTION

The present invention is directed to a method for efficient microbial production of pyruvate and its derivatives, such as alanine and diacetyl. The method utilizes bacterial cells exhibiting reduced activity of at least one enzyme in the pyruvate dehydrogenase (PDH) complex of enzymes, compared to wild-type bacterial cells. The bacterial cells are cultured in the presence of a primary carbon source, preferably glucose, and a secondary carbon source such as acetate and/or ethanol. If desired, the bacterial cells can be cultured in the presence of an additional carbon source, preferably a compound that is part of the tricarboxylic acid cycle of the bacterial cell, such as succinate.

Preferably PDH activity in the bacterial cells is undetectable. In a particularly preferred embodiment of the invention, the method utilizes bacterial cells wherein the gene encoding at least one enzyme in the PDH complex of enzymes is knocked out.

When the method of the invention is employed to produce pyruvate, pyruvate is preferably produced in an amount of at least about 30 g/L, and the yield of pyruvate as a function of glucose consumed is preferably at least about 0.70.

Optionally the bacterial cells utilized in the method of the invention exhibit reduced phosphoenolpyruvate carboxylase (PEP carboxylase) activity or reduced pyruvate oxidase activity, or both, compared to wild-type levels.

The production of pyruvate and diacetyl according to the invention is not redox balanced and thus NADH will accumulate in the cells. In these embodiments, the bacterial cells can be further engineered exhibit increased or added NADH oxidase activity compared to wild-type levels in order to maintain redox balance. When the method of the invention is employed to produce diacetyl, the bacterial cells also preferably exhibit added or increased acetolactate synthase activity compared to wild-type cells.

The production of alanine according to the invention is redox balanced and NADH will not usually accumulate in the cells. Production of alanine can, however, be enhanced by utilizing bacterial cells that exhibit added or increased alanine dehydrogenase activity and/or reduced lactate dehydrogenase activity compared to wild-type cells.

DETAILED DESCRIPTION OF ILLUSTRATIVE EMBODIMENTS

The invention provides a process that utilizes bacterial cells for the production of the metabolite pyruvate. The cells are grown, preferably aerobically, in the presence of a primary carbon source such as the carbohydrate glucose, a secondary carbon source such as acetate or ethanol, and optionally a carbon source in the tricarboxylic acid (TCA) cycle such as succinate.

Figure 1A:
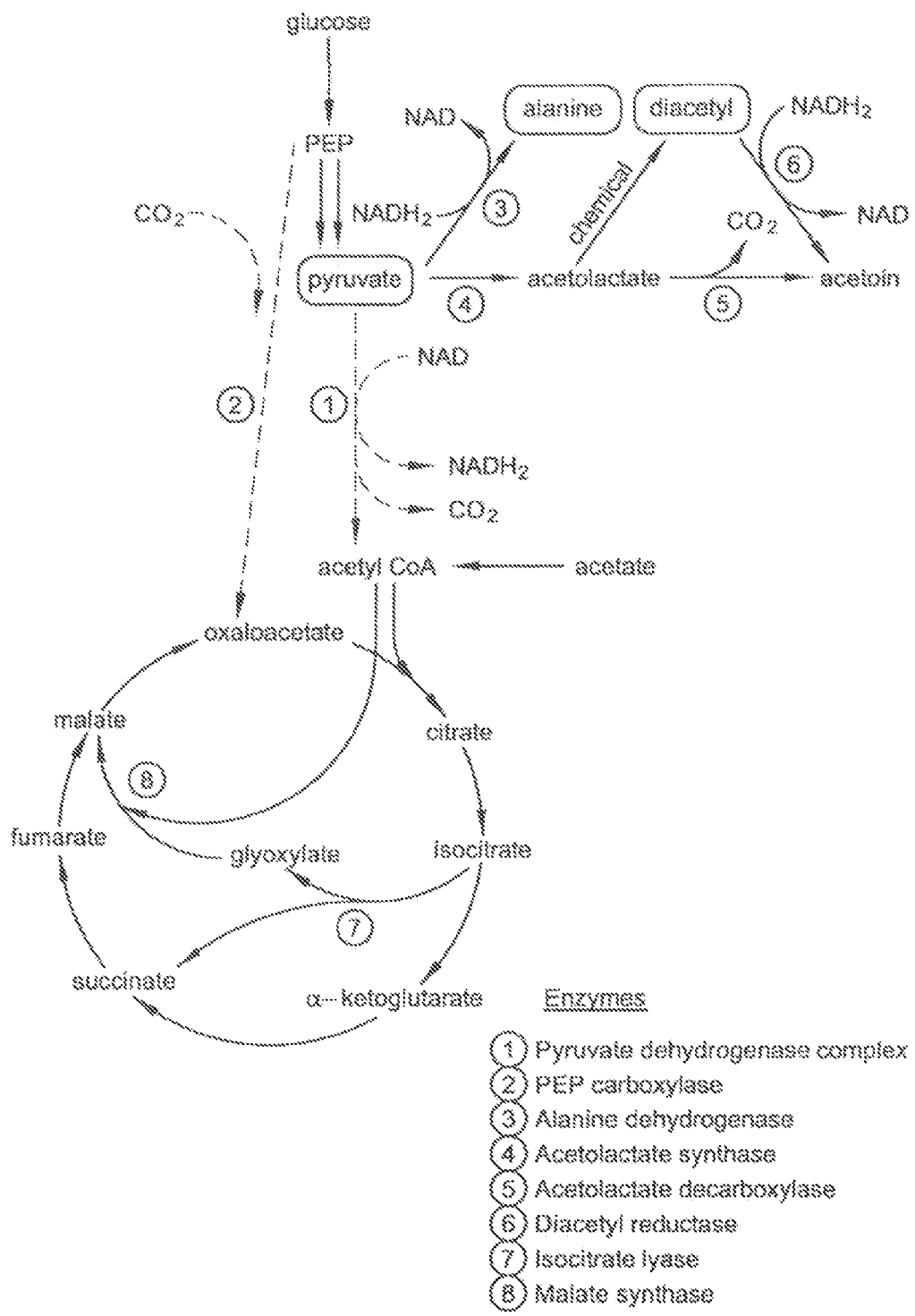
FIG. 1 illustrates (a) the biochemical pathways involved in the accumulation of pyruvate, alanine and diacetyl and (b) key enzymatic reactions in the production of pyruvate by *Escherichia coli* strains. Enzymes: 1, PEP carboxylase; 2, PEP synthase; 3, lactate dehydrogenase; 4, pyruvate oxidase; 5, pyruvate formate; 6, pyruvate dehydrogenase complex; 7, acetyl-CoA synthetase; 8, acetate kinase; 9, phosphotransacetylase (Zhu et al., Appl Environ Microbiol 74:6649-6655, 2008). Not all biochemical reactions or cofactors are shown.
Figure 1B:
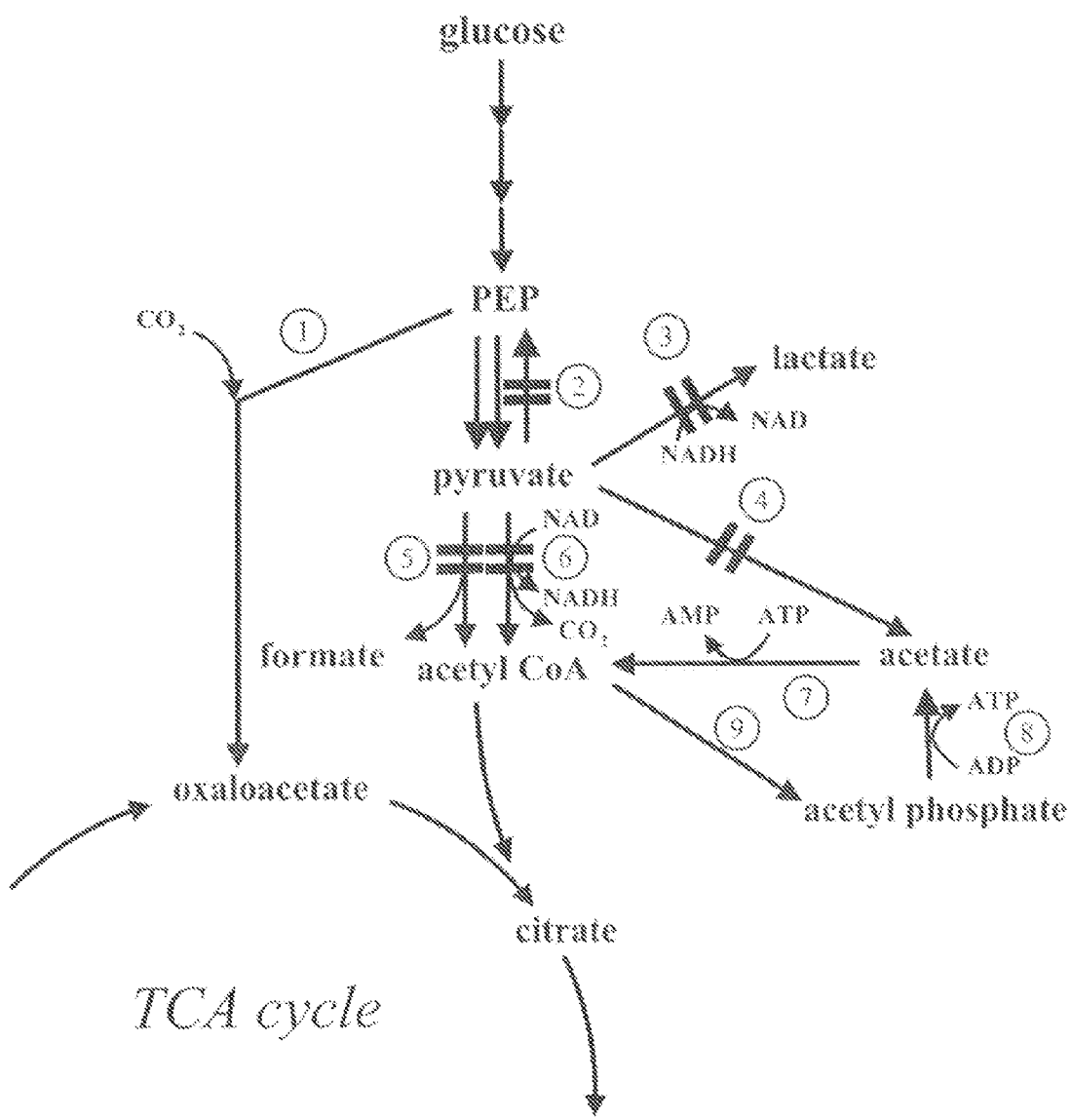
Figure 2A:
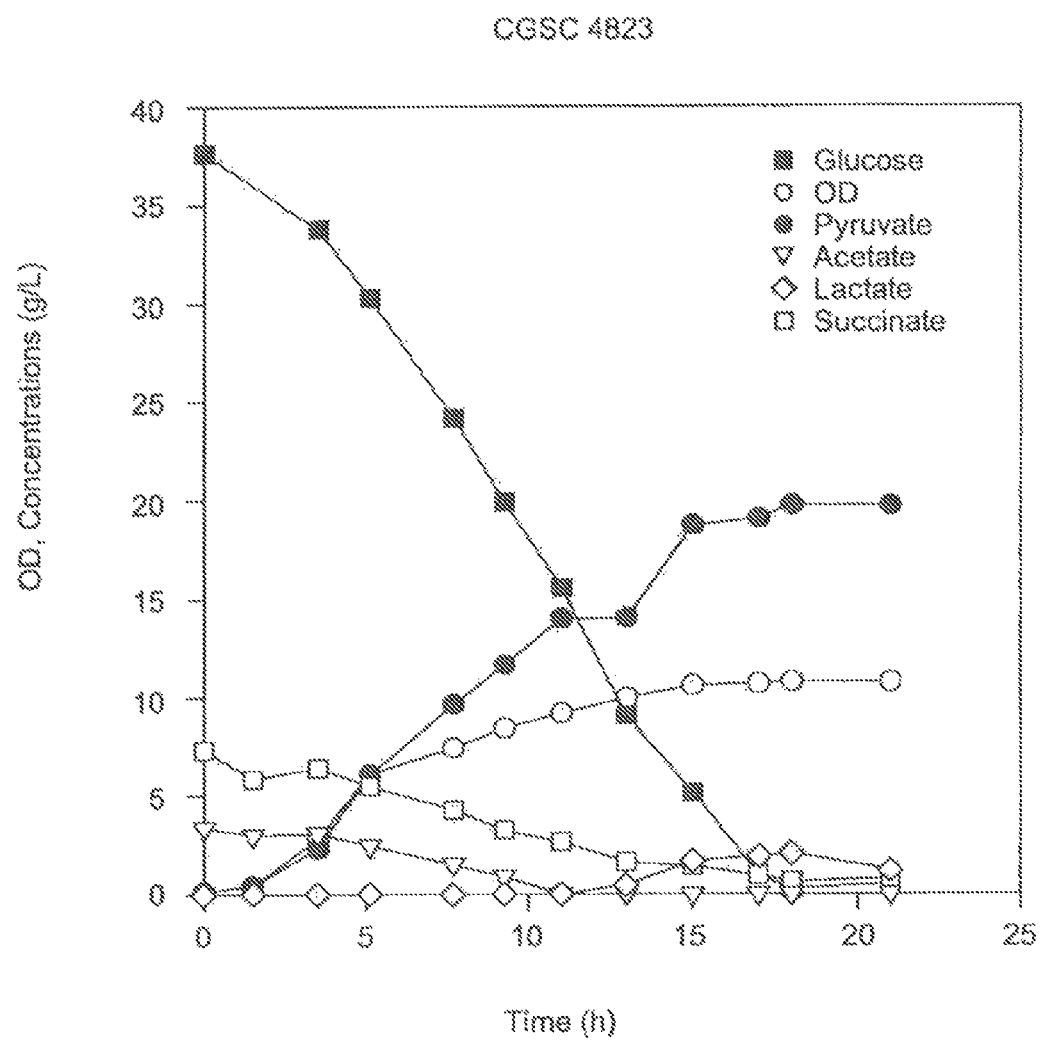
FIG. 2 shows graphs of cell growth, metabolite production and feed consumption as a function of time in fermentations using media C for strains (a) CGSC4823; (b) CGSC4823 Δppc; (c) CGSC6162; and (d) CGSC6162 Δppc.
Figure 2B:
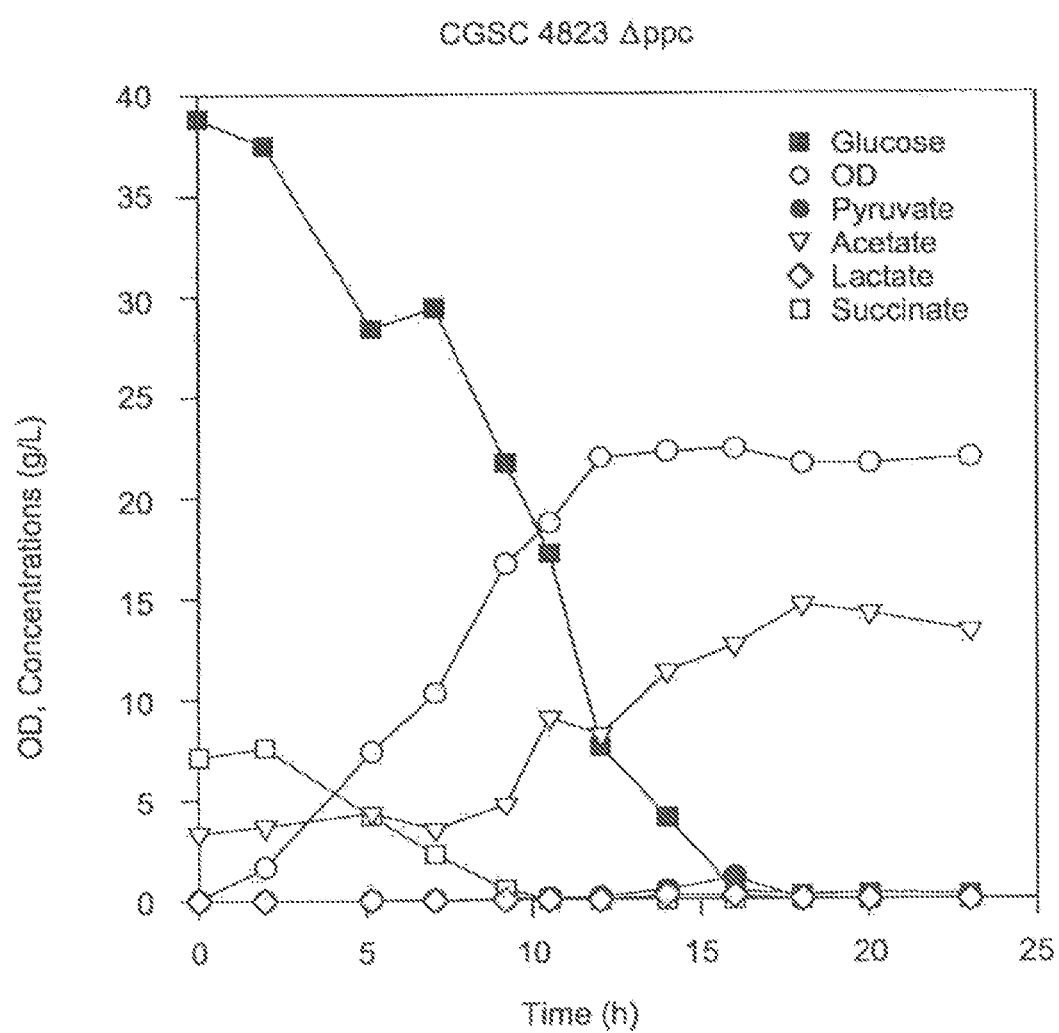
Figure 2C:
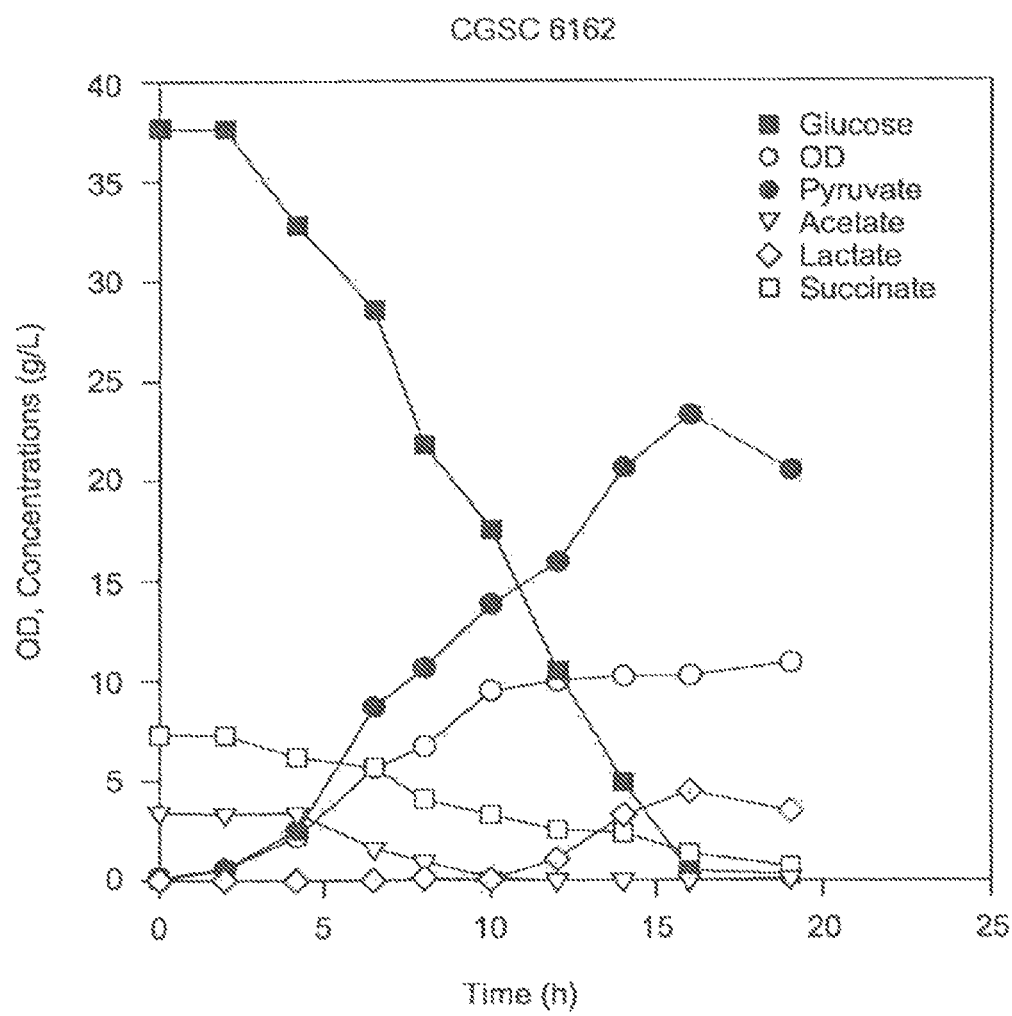
Figure 2D:
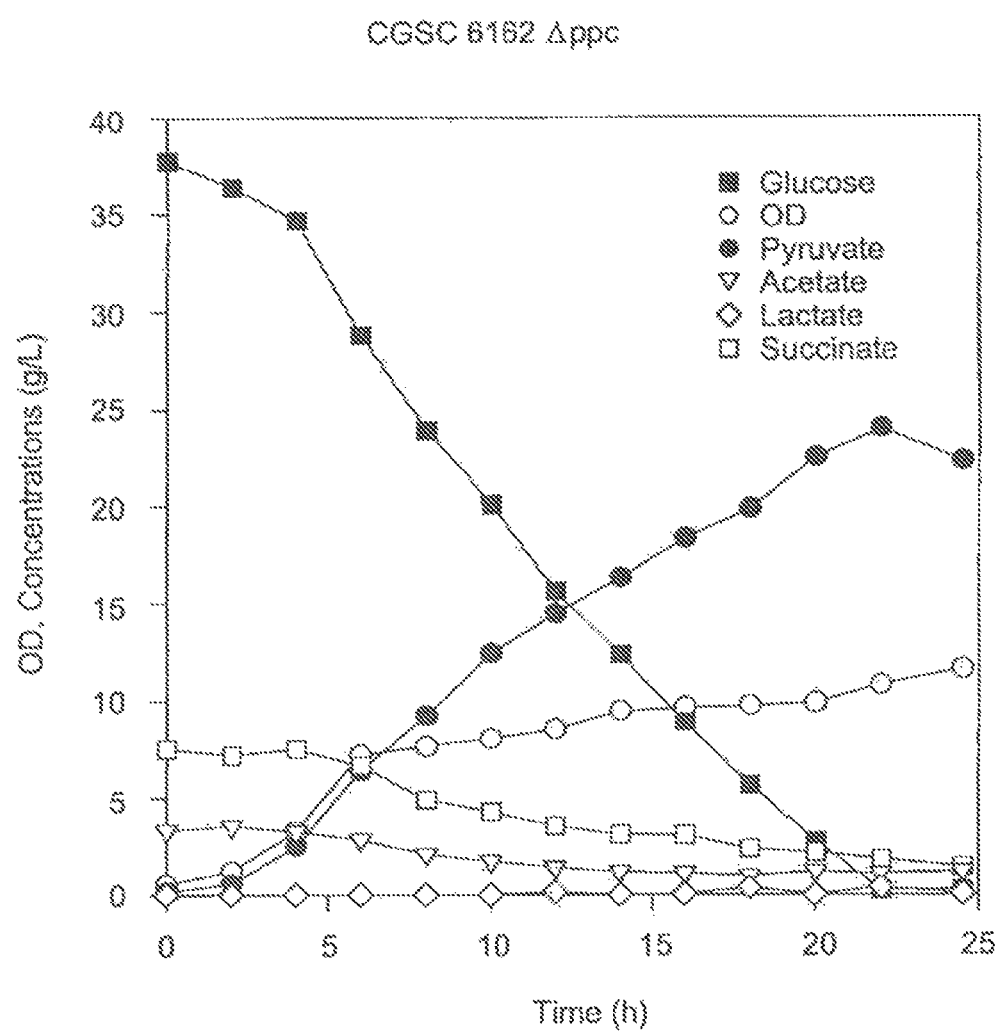

The process can also be used to produce metabolites derived from pyruvate (i.e., pyruvate derivatives), such as alanine and diacetyl. Metabolites "derived from" pyruvate or "pyruvate derivatives" are those biochemicals with respect to which pyruvate is a metabolic precursor in bacterial metabolism. In other words, the metabolic pathways for the production of biochemicals "derived from" pyruvate branch away from the glycolytic/TCA pathway at pyruvate. Examples of other products derived from pyruvate thus include 2,3 butanediol, acetoin, isoleucine and valine. The general microbial pathways for the synthesis of pyruvate and products derived from pyruvate are shown in FIG. 1.

The PDH complex includes pyruvate dehydrogenase, dihydrolipoamide acetyltransferase and dihydrolipoamide dehydrogenase. In *E. coli*, a preferred microbe for use in the invention, these enzymes are encoded by the aceE, aceF and lpd genes, respectively. The bacterial cells used in the method of the invention exhibit reduced activity of at least one enzyme in the pyruvate dehydrogenase (PDH) complex of enzymes compared to wild-type cells. This is referred to herein as reduced "PDH activity."

"Reduction" in an enzymatic activity compared to wild-type levels of that activity in a cell includes, but is not limited to, complete elimination of enzymatic activity. Thus, a reduction in PDH activity compared to wild-type levels of PDH activity includes, but is not limited to, complete elimination of PDH activity. Complete "elimination" of PDH activity encompasses a reduction of PDH activity to such an insignificant level that essentially no carbon flows from pyruvate to acetyl CoA. Preferably, the bacterial cells used in the method of the invention exhibit no detectable activity of at least one enzyme in the PDH complex during the entire period of fermentation. It should be understood that although the method of the invention is not limited by the way in which or the extent to which PDH activity is reduced in the bacterial cells, it is preferred that PDH activity be completely eliminated by disrupting the function of one or more genes associated with PDH activity. In a preferred method of the invention, bacterial cell growth surprisingly continues, with the concomitant production of pyruvate and its derivatives, even though PDH activity is completely eliminated.

Methods for reducing or eliminating PDH activity include those that act directly on the gene encoding one or more of the PDH enzymes, the mRNA transcript produced by the gene, the translation of the mRNA transcript into the protein, or the abolishment of the activity of the translated protein. One way the activity of an enzyme can be reduced is by physically altering the gene encoding the enzyme. For example, a gene encoding the enzyme can be mutated using site-directed mutagenesis to introduce insertions, deletions and/or substitutions. Alternatively, transcription of a gene can be impeded by delivering to the cell an antisense DNA or RNA molecule or a double stranded RNA molecule. Another way the activity of an enzyme can be reduced is by interfering with the mRNA transcription product of the gene. For example, a ribozyme (or a DNA vector operably encoding a ribozyme) can be delivered to the cell to cleave the target mRNA. Antisense nucleic acids and double stranded RNAs may also be used to interfere with translation. Antibodies or antibody-like molecules such as peptide aptamers can be used to abolish the activity of the translated protein. In general, methods that prevent production of an active PDH enzyme yield bacterial cells that are referred to as "gene knockouts" as the term is used herein.

Phosphoenolpyruvate carboxylase (PEP carboxylase) converts phosphoenolpyruvate (PEP), the metabolic precursor to pyruvate, to oxaloacetate and is encoded by the ppc gene. Accordingly, the bacterial cells used in the method of the invention are optionally further modified to reduce or eliminate the activity of PEP carboxylase. The invention is not intended to be limited by the method selected to reduce or eliminate PEP carboxylase activity.

Pyruvate oxidase converts pyruvate into acetate and is encoded by the poxB gene. Alternatively or in addition, the bacterial cells are further modified to reduce or eliminate the activity of pyruvate oxidase.

Phosphoenolpyruvate synthase (PEP synthase) converts pyruvate into phosphoenolpyruvate. Alternatively or in addition, the bacterial cells are further modified to reduce or eliminate the activity of PEP synthase.

Pyruvate formate lyase converts pyruvate into acetyl-CoA and formate. Alternatively or in addition, the bacterial cells are further modified to reduce or eliminate the activity of pyruvate formate lyase.

Hence, the method of the invention preferably utilizes bacterial cells exhibiting, compared to wild-type cells, reduced or no PDH activity (pdh$^-$) and, optionally, reduced or no pyruvate oxidase (pox$^-$), PEP carboxylase (ppc$^-$); PEP synthase, and/or pyruvate formate lyase activity.

In the presence of only glucose as the carbon source, bacterial cells deprived of PDH activity (so as to prevent conversion of pyruvate to acetyl CoA) and, optionally, PEP carboxylase (so as to prevent the precursor of pyruvate from being depleted) and, optionally, pyruvate oxidase (so as to prevent conversion of pyruvate to acetate) would certainly not be expected to grow, as these modifications adversely affect the ability of the cells to produce biochemical intermediates necessary for cell growth. In particular, complete removal of PDH activity would prevent cells from growing on glucose due to an inability to generate acetyl CoA, α-ketoglutarate and succinate, all necessary for cell growth.

The fact that the cells did grow when acetate was added as a co-substrate was surprising as those skilled in the art of bacterial fermentations view glucose as a preferred carbon source over acetate. O'Beirne et al., *Bioprocess Eng.* 23:375-380 (2000), discuss in detail the impact of acetate as a co-substrate in continuous cultivations of *E. coli*, and conclude that acetate has a noticeable inhibitory effect on the maximum specific growth rate and $CO_2$ evolution rate constant of *E. coli* even at low concentrations. It is thus especially surprising to discover that cells lacking PDH activity consume acetate, and grow well, when the preferred substrate glucose is also available; i.e., that glucose and acetate or ethanol will serve as simultaneous substrates.

Pyruvate, the endpoint of glycolysis, lies at an important metabolic branch point, or node (FIG. 1). The growth medium includes one or more primary carbon sources, typically glucose and/or glycerol but also including fructose, galactose, mannose, sucrose, lactose, arabiniose, and/or xylose. A primary carbon source is compound that is metabolically upstream from pyruvate and provides, directly or indirectly, a substrate for glycolysis. Reduction or elimination of PDH activity allows pyruvate to accumulate, but necessarily obstructs the flow of carbon from pyruvate to acetyl coenzyme A (acetyl CoA), thereby diverting carbon away from the TCA cycle. Thus the growth medium also includes at least one secondary carbon source that is metabolically downstream from the pyruvate node, for example, acetate, ethanol, or fatty acids. The secondary carbon source supplies carbon to acetyl CoA and the TCA cycle, and thus can be a compound that is part of the TCA cycle or a compound that facilitates carbon flux into the TCA cycle. The medium can contain a plurality of secondary carbon sources, such as acetate and a compound from the TCA cycle such as succinate in order to fully meet the requirements of the tricarboxylic acid (TCA) cycle.

When glycerol is used as a primary carbon source, acetate is preferably used as a secondary carbon source. More preferably, excess glycerol is used and the acetate is limited, leading to lower growth rates but more efficient formation of pyruvate from glycerol. Optionally, glucose is used as a second primary carbon source so that both acetate and glucose are limited, with glycerol in excess.

Glycerol is a readily available and inexpensive three-carbon by-product from the biodiesel fuel manufacturing process. Glycerol can serve as a carbon source for the microbial production of biochemicals, however microbial conversion of glycerol is less efficient than the conversion of sugars. To enhance the utilization of glycerol, both glycerol and glucose are provided as primary carbons sources, but glycerol is present in excess, and glucose provided in a limiting way, for example in a fed-batch process (see Example XII). The microbial rate of glycerol consumption was found to be higher when another primary carbon source, such as glucose, is present as a limiting substrate. The presence of some glucose increases the specific rate of product formation and the yield of a product from glycerol, and improves the overall process. Preferably, the amount of glucose in the culture is controlled so as to maximize production of the biochemical.

In a preferred embodiment, acetate is supplied as the secondary carbon source and is present as a limiting substrate. Acetate and glucose are preferably each present in the culture in limiting amounts compared to glycerol. In a preferred embodiment, the microorganism is an acetate auxotroph. The ratio of glucose to acetate is preferably less than 3:1, more preferably less than 2:1. The ratio of glycerol to acetate is less than 12:1, more preferably less than 9:1.

In preferred embodiments, the culture is operated as a chemostat, or as a fed-batch. The growth rate for the microorganism is preferably less than 0.15 $h^{-1}$. Preferred microorganisms for use in this embodiment of the method are bacteria such as *E. coli*. The microorganism can contain knockouts of any or all of the genes encoding for phosphoenolpyruvate synthase, lactate dehydrogenase, pyruvate formate lyase, a pyruvate dehydrogenase enzyme, pyruvate oxidase, or any combination thereof.

Example XII shows production of pyruvate using glycerol, glucose and acetate as carbon sources. A 20% increase in product yield from glycerol was observed, along with a volumetric productivity 60% greater than the productivity observed in the absence of glucose. Importantly, the increase in product generation was twice as much as the glucose that was provided: glucose addition facilitated glycerol utilization. Also, less $CO_2$ was generated in the presence of glucose, indicating less oxidation of substrates was necessary to meet energy requirements. Not only can both glycerol and glucose be consumed simultaneously, but these observations suggest a relatively small quantity of glucose in the presence of glycerol can meet precursor demands for a much more effective consumption of glycerol. This embodiment of the method is therefore expected significantly enhance the use of glycerol for the production of any microbial product. Numerous biodiesel industries that generate the by-product glycerol will be interested in producing additional fuels and chemicals.

In preferred embodiment, pyruvate production in the bacterial cells according to the method exceeds at least about 20 g/L, preferably about 30 g/L. Preferably the yield of pyruvate from glucose (grams of pyruvate produced per gram of glucose consumed) of at least about 0.70, more preferably at least about 0.75. Further, the volumetric productivity of pyruvate according to the method is at least about 1.0 g/liter-hour, more preferably at least about 1.5 g/liter-hour. Volumetric productivity is the pyruvate concentration (in g/L) divided by the fermentation time required to attain that concentration.

Regeneration of NAD is an important aspect in the aerobic growth of *E. coli* and other microorganisms. Glycolysis is possible only if NADH can be reoxidized since NAD is a necessary participant in the oxidation of glyceraldehyde-3-phosphate. Typically, under aerobic conditions, NADH is reoxidized by oxidative phosphorylation, a membrane-bound process which generates ATP.

To our surprise, when *E. coli* cells lacking PDH activity were cultured aerobically, lactate was formed. The formation of lactate suggested that the enzyme lactate dehydrogenase (LDH), normally observed in *E. coli* only under anaerobic conditions, may be active in these aerobic cultures. The production of lactate in the aerobic cultures further suggested that the cells are not able to oxidize NADH fast enough even though they are grown aerobically. Because the production of pyruvate and certain derivatives of pyruvate such as diacetyl is not redox-balanced, the cells will accumulate NADH during the operation of the method of the invention. As a result, the pyruvate yield is expected to improve if reoxidation of NADH is facilitated.

Overexpression of the enzyme NADH oxidase has been shown to result in diminished flux through lactate dehydrogenase (LDH) because of the removal of this enzyme's reduced cofactor NADH. Lopez DE Felipe et al. (*FEMS Microbiol. Lett.* 156:15-19 (1998)) constructed an NADH oxidase-overproducing *Lactococcus lactis* strain by cloning the *Streptococcus mutans* nox-2 gene, which encodes the $H_2O$-forming NADH oxidase. This engineered system allowed a nisin-controlled 150 fold overproduction of NADH oxidase resulting in decreased NADH/NAD ratio under aerobic conditions. In the presence of flavin adenine dinucleotide (FAD), a cofactor required for NADH oxidase activity, the lactate production was essentially abolished. Enhancing reoxidation of NADH is thus expected to be accompanied by a reduction in the formation of lactate, which is an undesirable product.

Optionally, therefore, the bacterial cells used in the method of the invention are further modified to increase the amount of NAD regenerated or the rate at which NAD is regenerated. NADH can also be directly oxidized using the nox gene which encodes NADH oxidase. *E. coli* cells (or other cells that lack the nox gene) that have been engineered to express additional NADH oxidase activity are referred to herein as having "added" NADH oxidase activity. It is expected that direct oxidation of NADH via NADH oxidase expression will result in diminished or possibly abolished flux toward lactate via LDH while ensuring the cells meet the demand of NAD. The presence of NADH oxidase activity is also expected to reduce the amount of lactate formed and therefore increase pyruvate yield. By increasing the availability of NAD, the presence of NADH oxidase activity is also expected to increase the rate of glucose uptake.

Therefore, in embodiments of the method used to produce products such as pyruvate or diacetyl which cause a net generation of NADH due to a redox imbalance, the bacterial cells are further optionally modified to increase the amount of, or rate at which, NAD is regenerated from NADH. Preferably, a gene encoding NADH oxidase (nox) is introduced into the bacterial cells. Such a gene can be introduced on a plasmid or other vector, or can be chromosomally integrated into the host genome.

A process that accumulates pyruvate is also expected to accumulate biochemicals that are a few enzymatic steps from pyruvate. For example, pyruvate is converted into alanine by a single enzyme, alanine dehydrogenase. For alanine production, therefore, the bacterial cells used in the method of the invention preferably overexpress alanine dehydrogenase (alaD) in addition to exhibiting reduced or eliminated PDH activity. As noted above, the bacterial cells can be further modified to reduce or eliminate the activity of pyruvate oxidase and/or PEP carboxylase.

The production of alanine is a redox-balanced synthesis in bacterial cells, hence it is not recommended to add or increase NADH oxidase activity. However, alanine production can also be enhanced by reducing or eliminating the activity of lactate dehydrogenase. Thus, the method for producing alanine optionally utilizes bacterial cells exhibiting, compared to wild-type cells, reduced or no lactate dehydrogenase activity (ldh⁻).

Diacetyl, another metabolite from pyruvate, can be produced by expressing or overexpressing acetolactate synthase in bacterial cells exhibiting reduced or eliminated PDH activity. Conversion of pyruvate to acetolactate, which is catalyzed by acetolactate synthase, is the first step in converting pyruvate to diacetyl. In a preferred embodiment, the bacterial cells used to produce diacetyl are *E. coli* cells that are preferably further modified to exhibit added or increased acetolactate synthase activity and/or added or increased NADH oxidase activity, and/or reduced or no activity of pyruvate oxidase and/or PEP carboxylase, as described above.

The present invention is illustrated by the following examples. It is to be understood that the particular examples, materials, amounts, and procedures are to be interpreted broadly in accordance with the scope and spirit of the invention as set forth herein.

EXAMPLES

Example I

Accumulation of Pyruvate in Defined Minimal Media by *E. Coli* Mutants Lacking PDH Activity Strains and Plasmids.

Strains and plasmids studied are listed in Table 1. The strains fell into two groups. Members of the first group were those that are blocked in their production of acetate. These strains can be classified as rpoS mutants (AJW1483, CGSC5024, CGSC6159), pta mutants (CGSC5992, CGSC7237), and ack mutants (CGSC5993, CGSC7238) (CGSC: *E. coli* genetic stock culture, Yale University). These strains were examined because it was hypothesized that they might accumulate pyruvate if carbon were prevented from entering the TCA cycle. Members of the second group were those that possess mutations in genes in the PDH complex (CGSC5518—a lpd mutant, CGSC4823—an aceE mutant, and CGSC6162—an aceF mutant).

TABLE 1

Strains used

| Name | Genotype | Reference/Source |
|---|---|---|
| MG1655 | wild-type (F$^-$ λ$^-$) | Guyer et al.,1980 |
| AJW1483 | gal hft Δ (rpoS::Kan) | Contiero et al., 2000 |
| CGSC4823 | aceE2 tyrT58(AS) trp-26 mel-1 | CGSC |
| CGSC5024 | F$^+$ λ- rpoS390(Am) rph-1 | CGSC |
| CGSC5518 | λ-lpd-1 trpA58 trpE61 | CGSC |
| CGSC5992 | λ-pta-39 iclR7(const) trpR80 | Guest, 1979 |
| CGSC5993 | λ-gal-2trpA9761(Am)iclR7(const)trpR72(Am) ack-11 | Guest, 1979 |
| CGSC6159 | λ- rpoS396(Am) rph-1 | CGSC |
| CGSC6162 | aceF10 fadR200 tyrT58(AS) adhE80 mel-1 | CGSC |
| CGSC7237 | λ-Δ (his-gnd)861 hisJ701 pta-200 | LEVine et al., 1980 |
| CGSC7238 | λ-Δ (his-gnd)861hisJ701ackA200 | LEVine et al., 1980 |

CGSC: *E. coli* Genetic Stock Center, Yale University

Media and Growth Conditions.

An initial comparison of strains expressing endogenous PEP carboxylase was conducted using defined minimal media modified from (Horn et al., *Appl. Microbiol. Biotechnol.* 46:524-534 (1996)) containing (in units of g/L): glucose, 30; $KH_2PO_4$, 6; $(NH_4)_2HPO_4$, 8; citric acid, 0.3; $MgSO_4 \cdot 7H_2O$, 1.5; $CaCl_2 \cdot 2H_2O$, 0.14; $Fe_2(SO_4)_3$, 0.0625; $H_3BO_3$, 0.0030; $MnCl_2 \cdot 4H_2O$, 0.0188; $Na_2EDTA \cdot 2H_2O$, 0.012; $CuCl_2 \cdot 2H_2O$, 0.0019; $Na_2MoO_4 \cdot 2H_2O$, 0.0031; $CoCl_2 6H_2O$, 0.0031; $Zn(CH_3COO)_2 \cdot 2H_2O$, 0.0099. Additionally, the media for CGSC 7237 and CGSC7238 contained 20 µg/L histidine; for CGSC4823, CGSC5518 and CGSC5993 the media contained 20 µg/L tryptophan; and for CGSC4823, CGSC5518 and CGSC6162 the media contained 1 g/L acetate. All the shake flasks were cultured at 37° C. with 250 rpm agitation.

Analytical Methods.

Cell growth was monitored by measuring the optical density (OD) at 600 nm (DU-650 UV-Vis spectrophotometer, Beckman Instruments), and this value was correlated to dry cell mass. Samples were analyzed for glucose, pyruvate, acetate, succinate and lactate quantitatively using a previous method (M. Eiteman et al., *Anal. Chin. Acta.* 338: 69-75 (1997)).

Comparison of Strains for Growth and Product Formation.

This example employed a metabolic engineering approach for the production of pyruvate. The strategy for generating pyruvate relied on preventing this biochemical intermediate from entering the TCA cycle or from being converted into acetate. We initially studied eleven different strains of *E. coli* for acetate and pyruvate accumulation and growth rate on glucose, looking for an absence of acetate accumulation and/or relatively high pyruvate accumulation. The initial specific growth rates were calculated from OD measurements, and the concentrations of by-products found after 10-20 hours of growth were used to calculate product yields (Table 2).

The strains having a mutation all had growth rates lower than the wild-type strain MG1655. In addition to the greatest growth rate, MG1655 generated no pyruvate, and accumulated acetate to a yield of 0.11. The three rpoS strains each behaved differently with AJW1483 generating both pyruvate and acetate, CGSC5024 generating neither pyruvate nor acetate, and CGSC6159 generating only acetate. Except for CGSC7237, the pta or ack strains generated some acetate. CGSC7237 and CGSC7238 accumulated significant pyruvate.

Of the strains with mutations in genes encoding for enzymes in the pyruvate dehydrogenase complex, the lpd strain CSGC5518 was unable to grow under the conditions studied. To our surprise, however, the aceE and aceF strains CGSC4823 and CGSC6162 accumulated the greatest concentrations of pyruvate, resulting in pyruvate yields of 0.32 g/g and 0.40 g/g, respectively.

TABLE 2

Comparison of *E. coli* Strains for Growth and Product Formation.
µ is the initial specific growth rate, $Y_{P/G}$ is the mass pyruvate yield on glucose and $Y_{A/G}$ is the mass acetate yield based on glucose.
Results are the means of triplicate experiments.

| Strain | µ (h − 1) | $Y_{P/G}$ (g/g) | $Y_{A/G}$ (g/g) |
|---|---|---|---|
| MG1655 | 1.57 | 0.00 | 0.11 |
| AJW1483 | 0.39 | 0.02 | 0.18 |
| CGSC4823 | 0.91 | 0.32 | * |
| CGSC5024 | 1.17 | 0.00 | 0.00 |
| CGSC5518 | 0.00 | — | * |
| CGSC5992 | 0.83 | 0.00 | 0.07 |
| CGSC5993 | 0.75 | 0.00 | 0.17 |
| CGSC6159 | 0.72 | 0.00 | 0.16 |
| CGSC6162 | 0.45 | 0.40 | * |
| CGSC7237 | 0.51 | 0.08 | 0.00 |
| CGSC7238 | 0.67 | 0.19 | 0.06 |

* media contained acetate at an initial concentration of 1.0 g/L

Example II

Accumulation of Pyruvate in Defined Minimal Media by *E. Coli* Mutants Lacking Both PDH and PEP Carboxylase Activity PEP carboxylase is the enzyme that converts PEP to oxaloacetate. This enzyme is believed not to be necessary for growth on acetate, and we reasoned it would serve only to decrease the yield of pyruvate by siphoning off its metabolic precursor PEP.

PEP carboxylase (ppc) mutants were generated from each of the five strains that accumulated pyruvate or that did not generate acetate: CGSC4823, CGSC5024, CGSC6162, CGSC7237, and CGSC7238. As noted in Example I, CSGC4823 is an aceE mutant (genotype: aceE2 tyrT58(AS) trp-26 mel-1) and CGSC6162 is an aceF mutant (aceF10 fadR200 tyrT58(AS) adhE80 mel-1). As discussed in Example I, CGSC6162 accumulates significant pyruvate even without additional genetic modification and under non-optimized conditions.

To construct these ppc mutants, a P1 lysate from JCL1242 (λ-F-Δ(argF-lac)U169 ppc::Kan) was used to transduce each strain to Kan(R) (Chao et al., *Appl. Env. Microbiol.* 59:4261-4265 (1993)). Because these ppc strains lacked the anaplerotic enzyme PEP carboxylase, the media as described in Example I was supplemented additionally with both acetate and succinate. The acetate and succinate were supplied at initial concentrations of either 0.62 g/L or 4.0 g/L each. The purpose of this study was to determine the effect of ppc deletion on growth rate and pyruvate formation, and the results are shown in Table 3.

TABLE 3

Comparison of *E. coli* ppc strains for growth rate. μ is the initial specific growth rate, $Y_{P/G}$ is the mass pyruvate yield based on glucose and $Q_P$ is the volumetric productivity of pyruvate.

| Strain | Initial Succinate and Acetate (g/L) | μ (h − 1) | $Y_{P/G}$ (g/g) | $Q_P$ (g/Lh) |
|---|---|---|---|---|
| CGSC4823 Δppc | 0.62 | 0.03 | 0.14 | 0.03 |
|  | 4.0 | 0.04 | 0.08 | 0.03 |
| CGSC5024 Δppc | 0.62 | 0.03 | 0.07 | 0.02 |
|  | 4.0 | 0.04 | 0.00 | 0.00 |
| CGSC6162 Δppc | 0.62 | 0.04 | 0.76 | 0.28 |
|  | 4.0 | 0.13 | 0.72 | 0.15 |
| CGSC7237 Δppc | 0.62 | 0.12 | 0.06 | 0.01 |
|  | 4.0 | 0.05 | 0.00 | 0.00 |
| CGSC7238 Δppc | 0.62 | 0.11 | 0.11 | 0.03 |
|  | 4.0 | 0.05 | 0.00 | 0.00 |

Deletion of the ppc gene resulted in slower growth rates and generally more pyruvate accumulation than the strains with ppc gene. Except for CGSC6162 Δppc, the maximum cell-mass produced with 4.0 g/L initial concentrations was considerably higher (~2 times) than with 0.62 g/L.

Strains CGSC5024 Δppc, CGSC7237 Δppc, and CGSC7238 Δppc did not consume acetate when grown on 0.62 g/L initial concentrations and in fact generated additional acetate once succinate was consumed. These three strains also did not accumulate pyruvate with 4.0 g/L initial concentrations and had the three lowest pyruvate yields with 0.62 g/L initial concentrations.

CGSC4823 Δppc and CGSC6162 Δppc accumulated significant pyruvate under both initial conditions. CGSC4823 Δppc produced less pyruvate than CGSC6162 Δppc and also accumulated acetate. CGSC6162 Δppc did not accumulate acetate. A small amount of lactate generation was also observed with strains CGSC4823 Δppc and CGSC6162 Δppc. From this study CGSC4823 Δppc and CGSC6162 Δppc were selected for the fermenter studies.

Example III

Accumulation of Pyruvate in Rich Medium by *E. Coli* Mutants Either Lacking PDH Activity or Lacking Both PDH and PEP Carboxylase Activity Strains and Plasmids.

The strains studied were among those listed in Table 1 in Example I. The strains included an rpoS mutant (CGSC5024), pta mutant (CGSC7237), ack mutant (CGSC7238) and a representative mutant for each of the three genes of the PDH complex, aceE, aceF and lpd (CGSC4823, CGSC6162, CGSC5518, respectively). A Δppc mutation was introduced into each of these strains as described in Example II.

Media and Growth Conditions.

An initial comparison of strains was conducted using 100 mL of media containing (g/L): glucose, 10.0; acetic acid, 3.0; succinic acid, 6.0; yeast extract, 2.5; tryptone, 5.0; $KH_2PO_4$, 6.0; $(NH_4)_2HPO_4$, 8.0; citric acid, 0.3; $MgSO_4 \cdot 7H_2O$, 1.5; $CaCl_2 \cdot 2H_2O$, 0.14; $Fe_2(SO_4)_3$, 0.0625; $H_3BO_3$, 0.0038; $MnCl_2 \cdot 4H_2O$, 0.0188; $Na_2EDTA \cdot 2H_2O$, 0.012; $CuCl_2 \cdot 2H_2O$, 0.0019; $Na_2MoO_4 \cdot 2H_2O$, 0.0031; $CoCl_2 \cdot 6H_2O$, 0.0031; $Zn(CH_3COO)_2 \cdot 2H_2O$, 0.0099. All the 500 mL shake flasks were cultured in duplicate at 37° C. with 250 rpm agitation and initial pH of 7.0.

Subsequent studies of selected strains were conducted in computer-controlled fermentations of 1.5 L volume carried out in 2.5 L fermenters (Bioflow III, New Brunswick Scientific Co., Edison, N.J.). Unless otherwise stated, the temperature was maintained at 37° C., agitation at 750 rpm, sterile filtered air was sparged at a rate of 1.5 L/min, and 20% NaOH and 20% HCl were used to control pH. The level of aeration ensured that the dissolved oxygen never fell below 30% of saturation for any of the fermentations. Samples were taken periodically and stored at −20° C. for subsequent analysis. The medium was identical to that described above except for initial concentration of 40 g/L glucose. For fed batch fermentations, glucose concentration was maintained at 3 g/L by automatic feeding of a 600 g/L glucose solution (YSI, Yellow Springs, Ohio).

Comparison of Strains for Growth and Product Formation.

This example employed a metabolic engineering approach for the production of pyruvate. The strategy for generating pyruvate relied on preventing this biochemical inter mediate from entering the TCA cycle or from being converted into acetate. Therefore, we initially studied six strains of *E. coli* and their corresponding ppc mutants for growth and acetate and pyruvate accumulation using a medium containing 10 g/L glucose. For all these strains, the glucose was exhausted in 7-10 hours. Table 4 summarizes the results of these duplicate shake flask fermentations, with pyruvate and acetate yields calculated at the time that glucose was exhausted.

TABLE 4

Pyruvate and acetate mass yields in strains of *Escherichia coli*.

| Strain | Max. OD | $Y_{P/G}$ | $Y_{A/G}$ |
|---|---|---|---|
| CGSC4823 | 8.1 | 0.54 | −0.01* |
| CGSC4823 Δppc | 5.1 | 0.097 | 0.19 |
| CGSC5024 | 8.8 | 0.085 | 0.34 |
| CGSC5024 Δppc | 4.7 | 0.12 | 0.28 |
| CGSC5518 | 6.1 | 0.31 | 0.11 |
| CGSC5518 Δppc | 8.0 | 0.083 | 0.30 |
| CGSC6162 | 6.8 | 0.47 | 0.030 |
| CGSC6162 Δppc | 6.9 | 0.41 | 0.029 |
| CGSC7237 | 6.7 | 0.34 | 0.024 |
| CGSC7237 Δppc | 5.5 | 0.11 | 0.30 |
| CGSC7238 | 7.0 | 0.25 | 0.17 |
| CGSC7238 Δppc | 5.3 | 0.10 | 0.23 |

$Y_{P/G}$: pyruvate generated/glucose consumed (g/g)
$Y_{A/G}$: acetate generated/glucose consumed (g/g)
*For this growth condition and time interval, the organism consumed acetate Strains with alterations in acetate synthesis included CGSC5024 (rpoS), CGSC7237 (pta) and CGSC7238 (ack). Of these CGSC7237 and CGSC7238 accumulated greater than 25% (mass yield) pyruvate, but only CGSC7237 generated less than 15% acetate. Introduction of the ppc mutation increased pyruvate accumulation only with CGSC5024, the lowest pyruvate producer. With CGSC7237 a ppc mutation increased acetate yield twelve-fold and decreased pyruvate yield three-fold. For all three strains a deletion in ppc substantially reduced the maximum cell concentration and hence cell yield. Strains with mutations in the PDH complex included CGSC4823 (aceE), CGSC6162 (aceF) and CGSC5518 (lpd). Each of these strains initially consumed acetate, accumulated significant pyruvate and began accumulating acetate after 2-4 hours. By the time glucose was exhausted, only CGSC4823 had a small net consumption of acetate. Introduction of the ppc mutation decreased pyruvate yield for all three strains, and increased acetate yield in the CGSC4823 and CGSC5518. A deletion in ppc increased cell yield for CGSC5518, decreased the cell yield for CGSC4823, and had no effect on cell yield in CGSC6162.

Example IV

Batch Fermentation Studies on CGSC4823, CGSC4823 Δppc, CGSC6162 and CGSC6162 Δppc CGSC4823 Δppc and CGSC6162 Δppc, along with their parent strain (CGSC4823 and CGSC6162) were grown at 1.5 L (initial volume) in a 2.5 L fermenter (New Brunswick Scientific Instruments, NJ) at 37° C. and 750 rpm with 1.5 L/min constant air flowrate using three different media (Media A, Media B and Media C). The modified Horn medium (Example I) was again used but with different initial concentrations of various carbon sources. Medium A contained 20 g/L glucose, 1 g/L acetate and 2 g/L succinate. Medium B contained 40 g/L glucose, 3 g/L acetate and 6 g/L succinate. Medium C contained 40 g/L glucose, 3 g/L acetate, 6 g/L succinate, 2.5 g/L yeast extract and 5 g/L tryptone. When the glucose concentration decreased to 3.0 g/L, it was controlled at this concentration by the automatic feeding of a 600 g/L glucose solution using an on-line glucose analyzer (YSI Instruments, OH). Samples were taken periodically during growth and stored at −20° C. for subsequent analysis. Analytical methods were as in Example I.

The results are shown in Table 5. Cells generally grew to their lowest cell mass in media A because of the lower concentrations of acetate and succinate in the media. Supplementing the media with yeast extract and tryptone (Media C) reduced the lag phases and generally increased the growth rates. FIG. 2 shows the products of fermentations using Media C and the strains (a) CGSC4823, (b) CGSC4823 Δppc, (c) CGSC6162 and (d) CGSC6162 Δppc, respectively. In these fermentations the pyruvate yield was greater than 0.50 except for CGSC4823 Δppc. Very small amounts of lactate were observed in CGSC4823 Δppc and CGSC6162 Δppc. From this study, CGSC6162 and CGSC6162 Δppc were selected for further fed-batch fermentation studies using Media C.

TABLE 5

Comparison of E. coli strains for growth rate and product formation when grown on different media. μ is the initial specific growth rate, $Y_{P/G}$ is the mass pyruvate yield based on glucose and $Q_P$ is the volumetric productivity of pyruvate.

| Strain | Media | μ ($h^{-1}$) | Max. OD | Max. Pyr. (g/L) | $Y_{P/G}$ (g/g) | $Q_P$ (g/Lh) |
|---|---|---|---|---|---|---|
| CGSC4823 | A | 0.18 | 4.1 | 9.8 | 0.58 | 0.28 |
| | B | 0.10 | 5.0 | 17.0 | 0.46 | 0.29 |
| | C | 0.20 | 11.0 | 20.0 | 0.52 | 1.10 |
| CGSC4823 Δppc | A | 0.08 | 2.2 | 10.0 | 0.63 | 0.10 |
| | B | 0.04 | 7.5 | 16.0 | 0.41 | 0.29 |
| | C | 0.07 | 22.3 | 1.1 | 0.03 | 0.06 |
| CGSC6162 | A | 0.17 | 7.2 | 11.0 | 0.56 | 0.69 |
| | B | 0.11 | 13.0 | 18.0 | 0.53 | 0.56 |
| | C | 0.11 | 10.0 | 23.0 | 0.63 | 1.50 |
| CGSC6162 Δppc | A | 0.03 | 0.7 | 3.7 | 0.91 | 0.09 |
| | B | 0.02 | 0.4 | 0.4 | — | — |
| | C | 0.19 | 11.0 | 24.0 | 0.64 | 1.10 |

Media A: 20 g/L glucose, 1 g/L acetate, 2 g/L succinate
Media B: 40 g/L glucose, 3 g/L acetate, 6 g/L succinate
Media C: 40 g/L glucose, 3 g/L acetate, 6 g/L succinate, 2.5 g/L yeast extract, 5 g/L tryptone Example V Fed-Batch Fermentation Studies on CGSC6162 and CGSC6162Δppc to Study the Effect of pH We next conducted fed-batch fermentations with CGSC6162 and CGSC6162 Δppc to study the affect of pH on pyruvate accumulation. The fermentations again commenced at a pH of 7.0 with a glucose concentration of 40 g/L. After 12 hours of growth, the pH was shifted (over the course of about 30 minutes) to the desired constant pH. When the glucose concentration reached 3.0 g/L (at 16-18 hours), glucose was maintained at that concentration until the fermentations terminated at 36 hours. Table 6 shows the mean specific rates of glucose consumption and formation for the three products at the pH levels studied over the time interval of 12 hours to 36 hours. The results include the specific activities of LDH and POX at 20 hours.

The pH had a significant effect on the CGSC6162 fermentations. At the lowest pH (6.0), glucose consumption was low, and acetate was the exclusive product (with a mass yield of 67%, essentially the theoretical maximum). Also, the activity of POX was relatively high. At the other three levels of pH (6.5, 7.0, 7.5), additional acetate did not form, pyruvate was the primary product, but lactate formation was also significant. The activity of POX was 3-4 times lower than observed at a pH of 6.0. For all CGSC6162 fermentations during the initial phase (pH 7.0 until 12 hours), pyruvate mass yield was approximately 70%. Thereafter the pyruvate yield decreased with time. For example, during the interval 12-20 hours, the yields were 59% (pH of 6.5), 72% (7.0), 52% (7.5), while during the interval 20-28 hours the yields were 25% (6.5), 32% (7.0), 38% (7.5). In the pH range of 6.5-7.5, lactate accumulated only after the acetate was exhausted. The maximum pyruvate concentration achieved was about 35 g/L for the fermentations continuously at a pH of 7.0.

For the CGSC6162 Δppc fermentations at the lowest pH of 6.0, the pyruvate that had been formed during the first 12 hours at a pH of 7.0 was partly consumed. Acetate was the exclusive product, and the POX activity was high. At pH values of 6.5 and 7.0, acetate was still formed, but pyruvate was the principal product and POX activity was about half that observed at a pH of 6.0. At a pH of 6.5 and 7.0, the POX activity was about two times greater in CGSC6162 Δppc than in CGSC6162. For the CGSC6162 Δppc fermentations during the initial phase (pH 7.0 until 12 hours), pyruvate mass yield was about 75% and again, the pyruvate yield decreased thereafter during the course of the fermentations. The LDH activity was low in all cases, did not correlate with lactate formation, and did not appear to follow any trend with pH.

TABLE 6

Specific rates of glucose consumption and pyruvate, acetate and lactate generation during fed-batch fermentations of CGSC6162 and CGSC6162 Δppc at different levels of pH. First 12.0 hours of growth occurred at a pH of 7.0, after which time the pH was gradually changed to indicated pH for an additional 24 hours and the rates recorded. Enzyme activities at 20 hours are in U/mg protein.

Figure 3A:
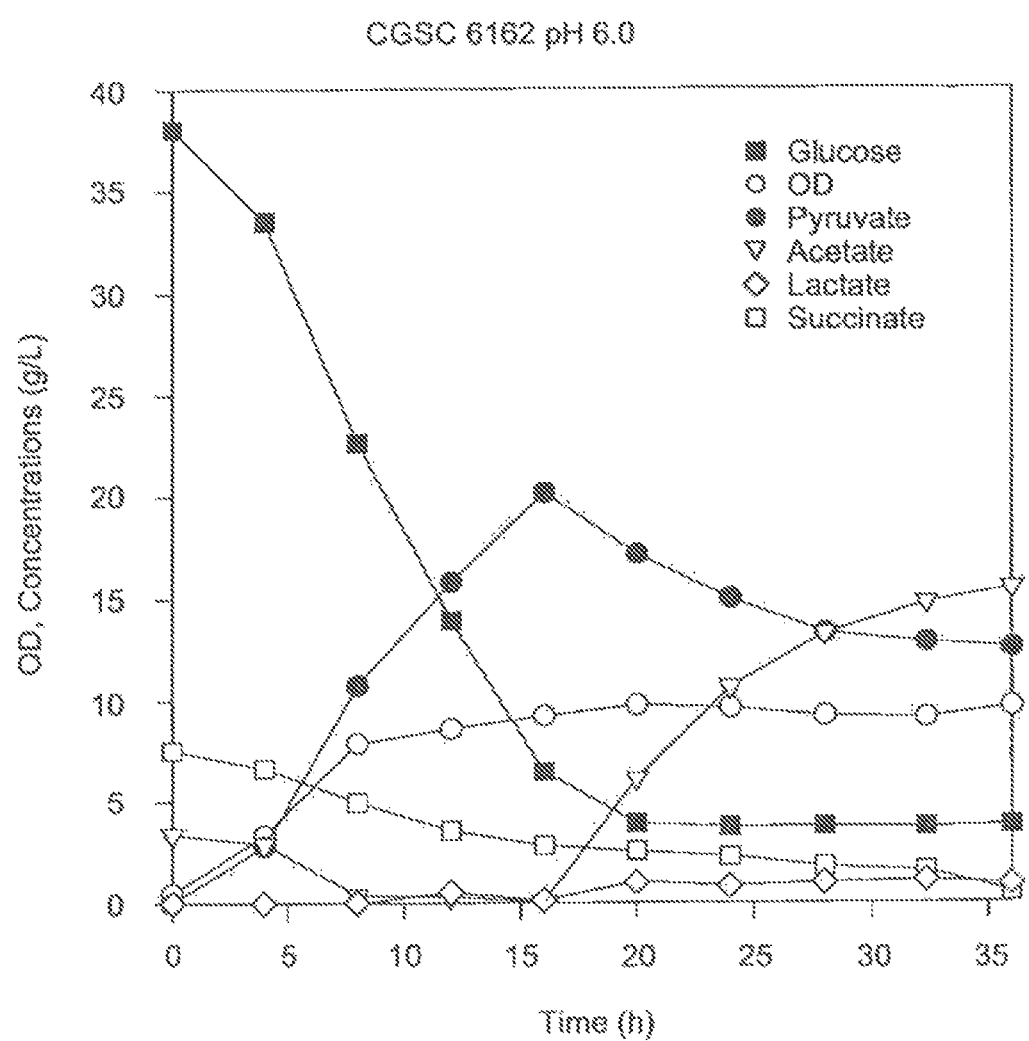
FIG. 3 shows graphs of cell growth, metabolite production and feed consumption as a function of time in fermentations using CGSC6162 at (a) pH of 6.0 and (b) pH of 7.0.
Figure 3B:
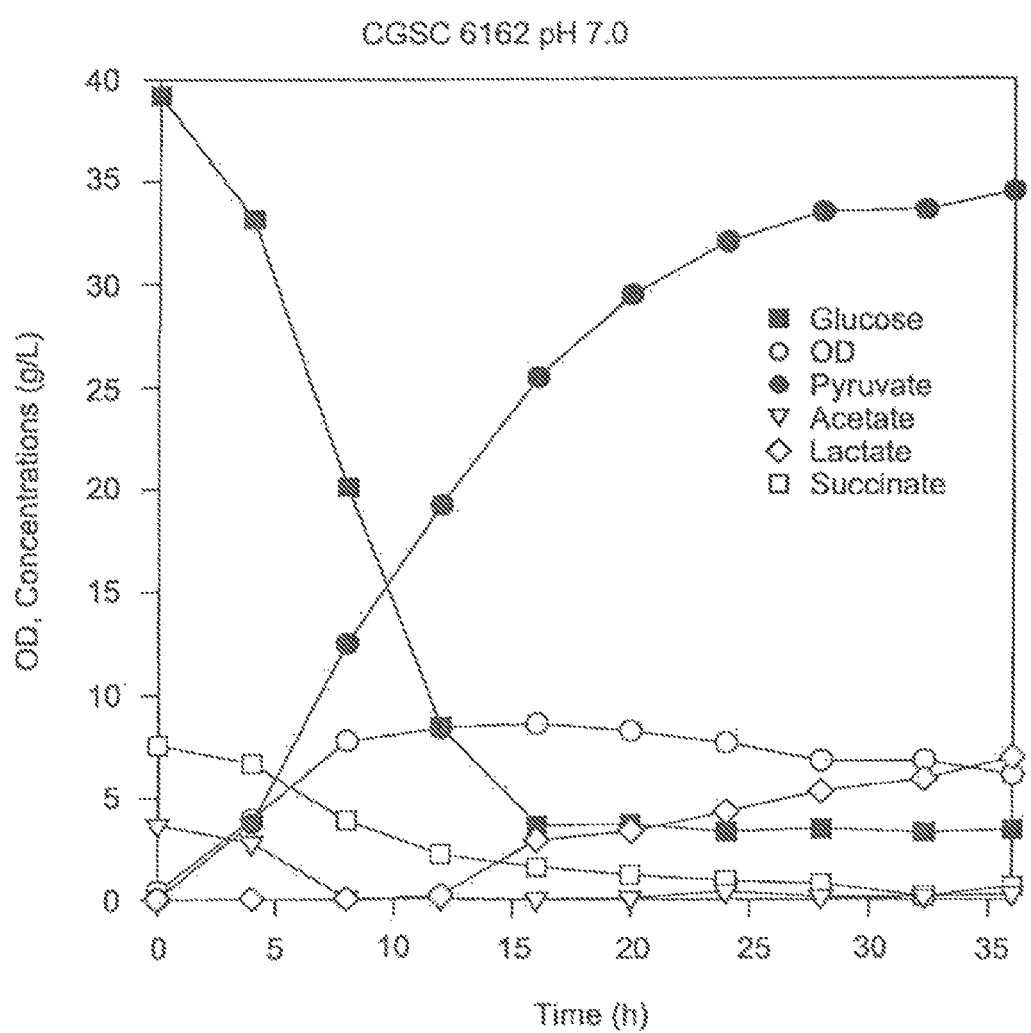

| Strain | pH | $q_G$ | $q_P$ | $q_A$ | $q_L$ | LDH | POX |
|---|---|---|---|---|---|---|---|
| CGSC6162 | 6.0 | 0.34 | 0 | 0.23 | 0 | 0.08 | 2.25 |
|  | 6.5 | 0.94 | 0.27 | 0 | 0.26 | 0.08 | 0.51 |
|  | 7.0 | 0.89 | 0.34 | 0 | 0.18 | 0.06 | 0.51 |
|  | 7.5 | 0.80 | 0.31 | 0 | 0.21 | 0.09 | 0.77 |
| CGSC6162 Δppc | 6.0 | 0.32 | −0.15* | 0.30 | 0 | 0.08 | 1.92 |
|  | 6.5 | 0.57 | 0.21 | 0.13 | 0 | 0.01 | 1.04 |
|  | 7.0 | 0.60 | 0.32 | 0.06 | 0.05 | 0.00 | 1.07 | q: specific rate of formation/consumption during the time interval of 12 hours to 36 hours (g compound/g cells hour)
*For this growth condition and time interval, the organism consumed this compound Several remarkable results are shown in FIG. 3. *E. coli* CGSC6162 did indeed simultaneously consume acetate and glucose. Interestingly, during the initial portion of these fermentations, these strains consumed all the acetate supplied, and the maximum concentrations of pyruvate occurred when the acetate concentration reached zero. Cell growth ceased when the acetate became depleted 8 hours after inoculation, demonstrating that this substrate was necessary for cell growth. Even though acetate was depleted in less than 10 hours, the cells generated well over 30 g/L pyruvate, and the mass yield of pyruvate from glucose was about 0.70 during the first 20 hours. The volumetric productivity during this time interval of low cell density was over 1.5 g/L hour.

After 20 hours, lactate surprisingly appeared as a co-product with acetate, with the concentration of pyruvate diminishing. Lactate (and NAD) generation from pyruvate (and NADH) by lactate dehydrogenase is known to be used by *E. coli* as a means to balance the cofactors NADH and NAD (Gokarn et al., *Appl. Env. Microbiol.* 66:1844-1850 (2000)). It therefore is particularly interesting that lactate was synthesized during this aerobic fermentation in which NADH could generate energy for the cell, as it suggests that NAD could not be regenerated from NADH quickly enough via oxidative phosphorylation to meet the demand of glucose uptake through the EMP pathway.

An interesting observation is that the generation of carbon dioxide was much lower than commonly observed in aerobic fermentations, which can be explained as follows. During the production of pyruvate which appears to have come from 70% of the glucose in our study, no carbon dioxide is generated from the conversion of glucose to pyruvate. One mole of carbon dioxide is generated from each mole of carbon entering the pentose phosphate pathway (likely less than 15% of the total glucose), and only a small quantity of carbon dioxide will be generated from the consumption of acetate through the TCA cycle, primarily for toward the synthesis of biomass.

The results demonstrate that a pyruvate yield exceeding 0.75 was routinely obtained during the first 12 hours of these fermentations. Moreover, the results demonstrate that changing the pH from 7.0 after 12 hours did not improve the pyruvate yield. Switching to a pH of 6.0 for both strains resulted in the consumption of pyruvate and generation of acetate. This utilization of pyruvate did not result in an increase in the cell mass concentration. FIG. 3(*a*) shows the fermentation using CGSC6162 at a pH of 6.0. FIG. 3(*b*) shows the fermentation using CGSC6162 at a pH of 7.0. In cases in which the pH remained at 7.0, the volumetric productivity of pyruvate at the time acetate was depleted was over 1.5 g/Lh. This is the first report of a viable industrial process for the production of pyruvate in *E. coli*, something that was heretofore thought impossible because of the complexities and interdependencies of the interrelated metabolic pathways that stem from the pyruvate node.

Example VI

Fed-Batch Fermentation Studies on CGSC6162 and CGSC6162Δppc to Study the Effect of Temperature Fed-batch fermentations of CGSC6162 and CGSC6162 Δppc were also studied at three different temperatures (32° C., 37° C. and 42° C.) at pH 7.0 for 36 hours. Pyruvate and lactate yields were calculated for two time intervals (0-20 hours; and 20-36 hours), and the results are shown in Table 7.

Figure 4:
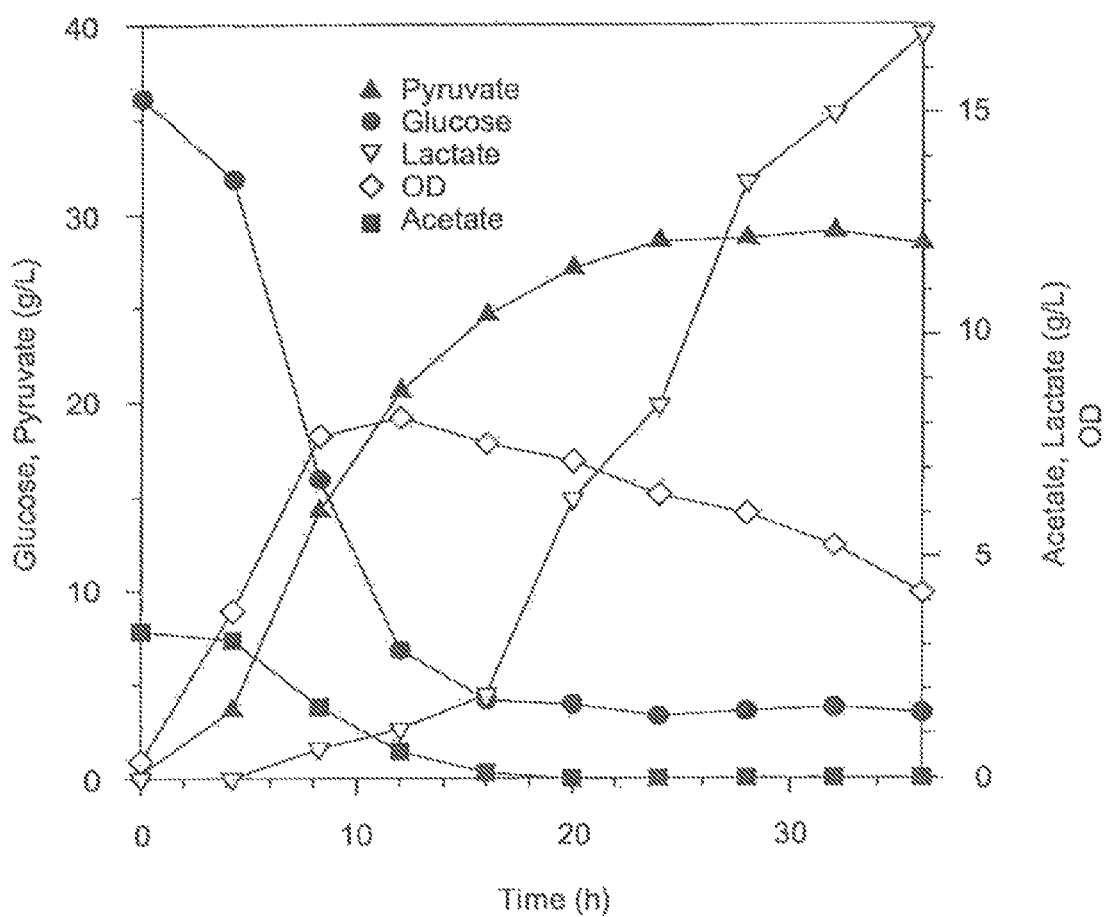
FIG. 4 shows a graph of fermentation as a function of time using CGSC 6162 at 42° C. and at a pH of 7.0.

CGSC6162 did not accumulate acetate at any temperature (FIG. 4 shows a 42° C. fermentation). Lactate and pyruvate production were strongly influenced by temperature. The initial rate of pyruvate formation was greatest at 42° C., with 21-25 g/L accumulating in 12 hours. However, after about 12 hours at this temperature, the cell density decreased, and CGSC6162 accumulated lactate instead of pyruvate. Thus, the greatest pyruvate concentrations and lowest lactate concentrations over the course of 36 hours were achieved when the fermentation temperature was maintained at 32° C.

Figure 5:
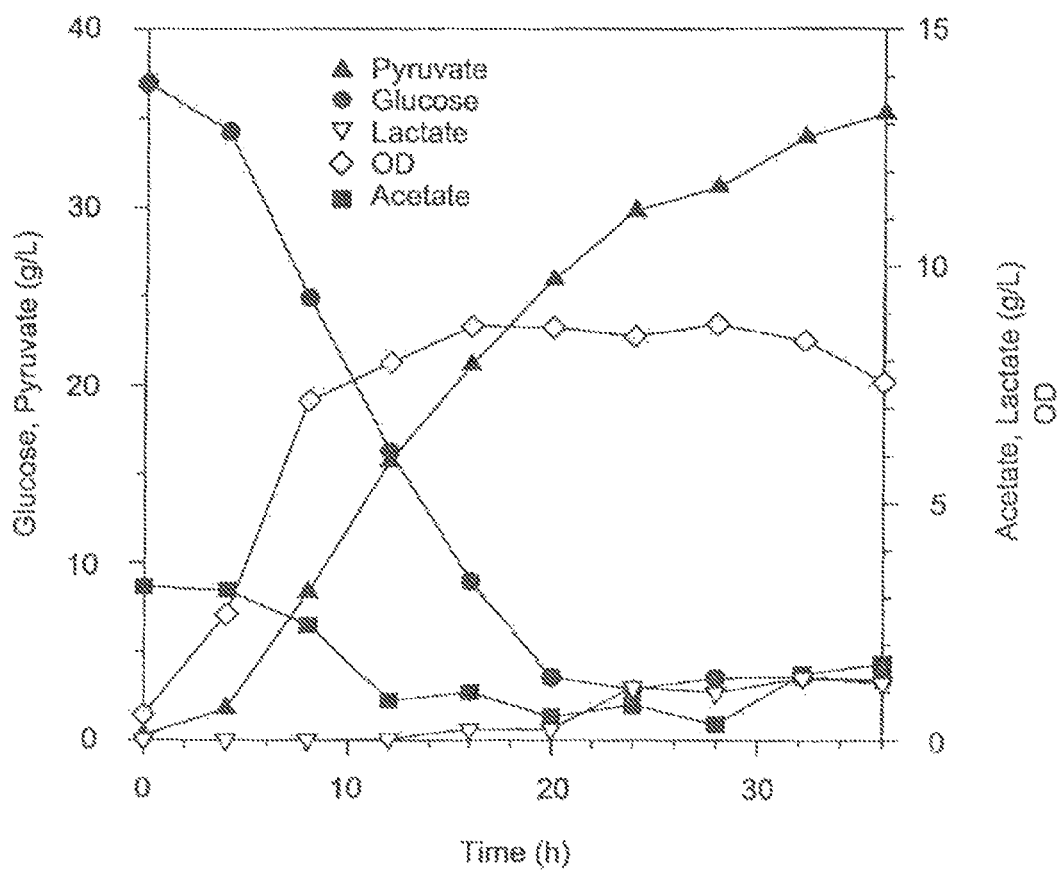
FIG. 5 shows a graph of fermentation as a function of time using CGSC 6162 Δppc at 32° C. and at a pH of 7.0.

Although initially CGSC6162 Δppc consumed acetate, this strain eventually accumulated acetate at all temperatures (FIG. 5 shows an example CGSC6162 Δppc fermentation at 32° C.). However, the accumulation of acetate was greater and commenced sooner at higher temperature. Specifically, at 42° C. acetate began accumulating at about 8 hours, at 37° C. acetate accumulation began at 12-16 hours, and at 32° C. acetate began accumulating after 20 hours. Similar to CGSC6162, with CGSC6162 Δppc lactate accumulation began after 12 hours for all temperatures. The rate of lactate production was again strongly temperature dependent, with higher temperature favoring lactate. This strain also achieved its maximum pyruvate concentration at 32° C.

Table 7 shows the specific activities of LDH and POX at 20 hours for the two strains at the three different temperatures. In all cases the LDH activity was low and did not follow a trend. POX activity tended to increase with increasing temperature in both CGSC6162 and CGSC6162 Δppc. Furthermore, POX activity was about twice as great

TABLE 7

Yields of pyruvate and lactate during fed-batch fermentations of CGSC6162 and CGSC6162 Δppc at different controlled temperatures. Yields are calculated during two time intervals (0-20 hours and 20-36 hours). Enzyme activities at 20 hours are in U/mg protein.

| Strain | Temp (° C.) | Maximum Pyruvate Concentration (g/L) | $Y_{P/G}$ 0-20 h | $Y_{P/G}$ 20-36 h | $Y_{L/G}$ 0-20 h | $Y_{L/G}$ 20-36 h | LDH | POX |
|---|---|---|---|---|---|---|---|---|
| CGSC6162 | 32 | 37 | 0.73 | 0.47 | 0.03 | 0.07 | 0.04 | 0.57 |
|  | 37 | 36 | 0.67 | 0.25 | 0.08 | 0.20 | 0.06 | 0.51 |
|  | 42 | 32 | 0.67 | 0.16 | 0.01 | 0.58 | 0.07 | 0.80 |

TABLE 7-continued

Yields of pyruvate and lactate during fed-batch fermentations of CGSC6162 and CGSC6162 Δppc at different controlled temperatures. Yields are calculated during two time intervals (0-20 hours and 20-36 hours). Enzyme activities at 20 hours are in U/mg protein.

| Strain | Temp (° C.) | Maximum Pyruvate Concentration (g/L) | $Y_{P/G}$ 0-20 h | $Y_{P/G}$ 20-36 h | $Y_{L/G}$ 0-20 h | $Y_{L/G}$ 20-36 h | LDH | POX |
|---|---|---|---|---|---|---|---|---|
| CGSC6162 Δppc | 32 | 35 | 0.70 | 0.60 | 0.01 | 0.07 | 0.01 | 0.45 |
| | 37 | 35 | 0.74 | 0.41 | 0.02 | 0.11 | 0.00 | 1.07 |
| | 42 | 29 | 0.57 | 0.25 | 0.06 | 0.60 | 0.01 | 1.58 |

$Y_{P/G}$: pyruvate generated/glucose consumed (g/g)
$Y_{L/G}$: lactate generate/glucose consumed (g/g)

in CGSC6162 Δppc than in CGSC6162 at 37° C. and 42° C. As the data indicates, the production of pyruvate may further be increased by deleting the pox gene.

Example VII

Overexpression of NADH Oxidase to Produce Pyruvate

The accumulation of small amounts of lactate during highly aerobic conditions (see Example V and VI) suggests that NADH is not being converted into NAD to keep pace with the demand of glycolysis. It would be of little benefit to delete lactate dehydrogenase activity as a means of producing pyruvate and avoiding lactate generation, as this does not address what appears to be the underlying cause, namely, the conversion of NADH to NAD. Furthermore, cells do not appear to be limited in ATP generation, since the NADH is being consumed toward lactate formation rather than via oxidative phosphorylation.

One way to enhance the regeneration of NAD is by introducing additional NADH oxidase activity into the strains. The nox gene encodes NADH oxidase which converts NADH and oxygen directly into NAD and water (without the generation of ATP). Known nox genes encoding for NADH oxidase include those from *Streptococcus pneumoniae, S. faecalis* and *Saccharomyces cerevisiae*. Lopez de Felipe et al. (*FEMS Microbiol. Lett.* 156:15-19 (1998)) have previously used NADH oxidase overexpression in *Lactococcus lactis* to significantly decrease the NADH/NAD ratio and reduce lactate synthesis. We have constructed a pTrc99A-nox plasmid which overproduces NADH oxidase from *S. pneumoniae*. This plasmid, which is inducible by the addition of IPTG, can be used to transform PDH and PDH+PEP carboxylase mutant strains to enhance the production of pyruvate.

Example VIII

Enhanced Production of Diacetyl

If pyruvate can accumulate significantly in cells, then biochemical derivatives of pyruvate might also accumulate in these cells. Diacetyl (2,3-butanedione), with a vapor pressure similar to ethanol, is a constituent of food and fruit aromas and is the main constituent of "butter aroma." As shown in FIG. 1, the synthesis of diacetyl first involves the conversion of pyruvate to acetolactate by the enzyme acetolactate synthase. Diacetyl can be synthesized from pyruvate by a two step process involving 1) the conversion of pyruvate to acetolactate by the enzyme acetolactate synthase and 2) the chemical oxidation/decomposition of acetolactate to diacetyl. These two additional pathways are shown in FIG. 1.

Plasmid pAAA215 overproduces acetolactate synthase from *Bacillus subtilis* (Aristidou et al., *Biotechnol. Bioeng.* 44:944-951 (1994)). The synthesis of this enzyme appears to be induced by cell growth and its activity is stimulated by the presence of acetate (Holtzclaw et al., *J. Bacteriol.* 121:917-922 (1975)). The product acetolactate itself is chemically unstable, being oxidized (by oxygen) to diacetyl in the presence of metal ions such as $Fe^{3+}$. Two competing biochemical reactions can also occur. In some organisms, acetolactate decarboxylase catalyzes the decarboxylation of acetolactate under oxygen limited conditions to acetoin. The chemical oxidation of acetolactate appears to be favored at a pH of about 5, while the enzymatic decarboxylation of acetolactate appears to be favored at a pH of about 6.5. The presence of acetolactate decarboxylase activity in *E. coli* has not been established. A second competing reaction involves the enzyme diacetyl reductase, whose activity has been observed in *E. coli*, which directly converts diacetyl to acetoin. This reaction has a pH optimum of about 7.0, and requires NADH or NADPH, the former being more active with the latter. Interestingly, acetate has been shown to inhibit the activity of this enzyme, 20 mM decreasing the activity by 35% (Ui, *Agr. Biolog. Chem.* 51:1447-1448 (1987)). Moreover, under highly oxygenated conditions, NADH and NADPH will normally be less prevalent than their oxidized analogues. The pH optima, the effects of acetate and oxygen, and the prospects for adding other chemical catalysts or inhibitors would suggest that a fermentation process to accumulate diacetyl is feasible under the general conditions we have previously observed for pyruvate generation.

To accomplish, this, the "best" strains as identified in Example I are transformed with the pAAA215 plasmid that overproduces acetolactate synthase from *B. subtilis* (Aristidou et al., *Biotechnol. Bioeng.* 44:944-951 (1994)). The plasmid pTrc99A-nox, which overproduces NADH oxidase, can also be transformed into these strains. Because they contain compatible replicons, both the pTrc99A-nox plasmid which overproduces NADH oxidase and the pAAA215 plasmid which overproduces acetolactate synthase can be introduced into the same cell. The pTrc99A-nox plasmid uses the colE1 replicon and is selected for using ampicillin while the pAAA215 plasmid uses the P15A replicon and is selected for using tetracycline. Numerous researchers have constructed dual plasmid strains like this where the first plasmid contained the colE1 replicon and the second plasmid contained the P15A replicon. The result is the construction of at least one strain with a PDH mutation and enhanced acetolactate synthase activity, and also a strain with additional increased NADH oxide activity.

The chemical production of diacetyl is promoted by oxidation. The conversion of diacetyl to acetoin by the undesirable enzymatic reaction (diacetyl reductase) uses NADPH or NADH as a cofactor with the former being preferred. We would expect a highly oxygenated environment to prevent this undesirable reaction. It does not appear feasible to perform a gene "knock out" of diacetyl reductase as evidence suggests that this reaction is carried out inadvertently (i.e., nonspecifically) by one or more general reductase enzymes. The presence of NADH oxidase should facilitate diacetyl production because, like pyruvate generation itself, a greater rate of NADH oxidation would tend to increase the rate of glucose uptake and reduce the availability of NADH/NADPH for side reactions.

Example IX

Enhanced Production of Alanine

Alanine can be synthesized from pyruvate in a single reaction step by the enzyme alanine dehydrogenase. L-alanine is generally produced by an enzymatic process in which L-aspartic acid is enzymatically decarboxylated (Ichiro et al., U.S. Pat. No. 3,458,400 (1969)). E. coli has activity in a racemase, which would convert the L-alanine produced in any process to D-alanine, resulting in a DL-alanine product. Although ultimately the activity of alanine racemase can be abolished to yield exclusively the L-alanine product, this example focuses on the production of the racemic mixture of alanine.

In order to test whether the same approach could be used to generate derivatives of pyruvate, such as alanine, we transformed CGSC6162 with the pTrc99A-alaD plasmid that we constructed which overproduces alanine dehydrogenase from *Bacillus sphaericus* (Ohashima et al., *Eur. J. Biochem.* 100: 29-39 (1979)). Alanine dehydrogenase is an enzyme that converts pyruvate to alanine. This strain was grown on media containing 25 g/L glucose, 3.0 g/L yeast extract, 6.0 g/L tryptone, 2.7 g/L succinate, 1 g/L acetate, 1 mg/L biotin, 1 mg/L thiamine HCl, 15 mg/L $CaCl_2 2H_2O$, 5.875 g/L $Na_2HPO_4$, 3.0 g/L $KH_2PO_4$, 6 g/L $NH_4Cl$ and 0.25 g/L $MgSO_4 7H_2O$. Continuous constant agitation (1000 rpm) and air flowrate (1.0 L/min) were used.

Figure 6:
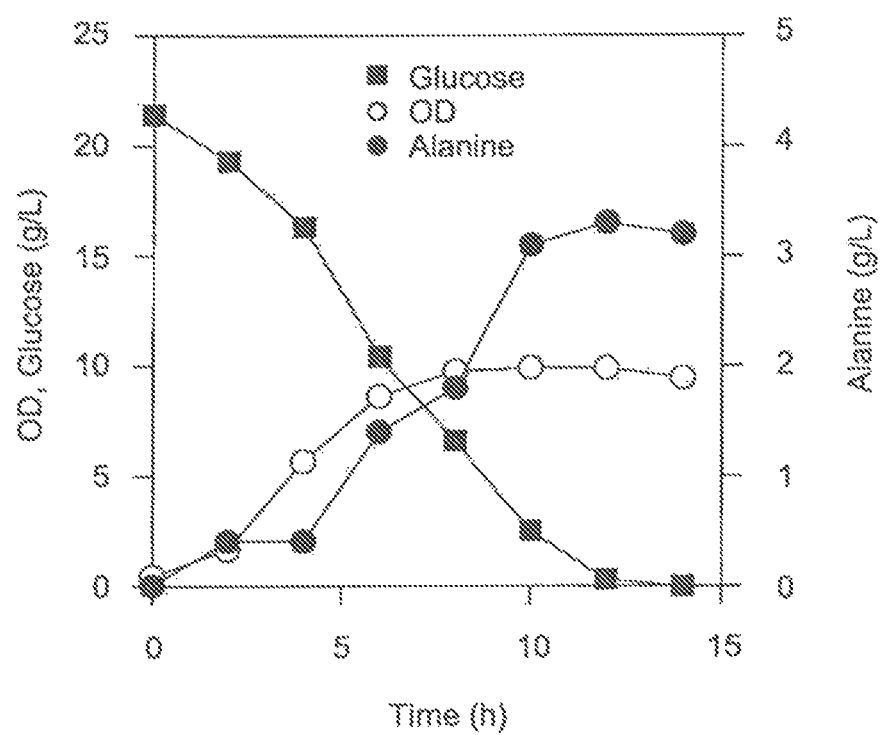
FIG. 6 shows a graph of cell growth, alanine production and glucose consumption as a function of time in a fermentation using CGSC6162 modified to overexpress the alaD gene from *Bacillus sphaericus*.

FIG. 6 shows the results, with alanine accumulating to 3.3 g/L. Alanine accumulated to this level even though the nitrogen concentration (as N) was less than 2 g/L in the initial media. This nitrogen would be required both for cell growth (about 12% N) and alanine synthesis (about 15% N). The activity of alanine dehydrogenase was 0.04 U/mg at 8 hours and 0.06 U/mg at 14 hours.

The formation of alanine consumes NADH in the final step via alanine dehydrogenase. Considering that the cell would otherwise generate ATP from the oxidative phosphorylation of NADH, and full aeration was used in our study with dissolved oxygen concentration always above 75% saturation, this level of accumulation is remarkable.

Interestingly, significant pyruvate still accumulated (10 g/L). This suggests that alanine production was limited due to a non-optimal amount of alanine dehydrogenase. The activity of alanine dehydrogenase in our system can be increased by recloning the *B. sphaericus* alaD gene into a pTrc99A derivative that we have constructed which expresses genes at a level 3-10 times higher than is obtainable in the original pTrc99A vector.

The biochemistry of alanine production has a crucial difference from the biochemistry of pyruvate production. The production of pyruvate from glucose generates 2 moles of NADH per mole of glucose, and should be conducted with high oxygenation so the NADH produced can be converted to ATP by oxidative phosphorylation. Moreover, oxygen limitation in this case could lead to activation of pyruvate formate lyase and subsequent reduction of pyruvate through fermentative regeneration of NAD. In contrast, the overall production of alanine from glucose does not generate NADH due to the final step from pyruvate to alanine. Since oxygenation affects the NADH/NAD balance, the availability of oxygen should be have a significant impact on alanine production. We expect that reduction of oxygen availability should improve alanine production until a level is reached where the fermentative enzymes such as lactate dehydrogenase and pyruvate formate lyase are induced. The oxidation "state" of the system can be most readily monitored by dissolved oxygen concentration or by the culture's redox potential.

Note that because alanine dehydrogenase consumes NADH, NADH production is balanced during the conversion of glucose to alanine. It would therefore be unnecessary, and indeed undesirable, to overexpress NADH oxidase to enhance the production of the pyruvate derivative alanine.

Example X

Enhanced Production of Alanine in a Lactate Dehydrogenase Mutant

Lactate dehydrogenase converts pyruvate to lactate and thus competes with alanine dehydrogenase, which converts pyruvate to alanine. The lactate dehydrogenase and alanine dehydrogenase enzymes both use pyruvate and NADH as substrates; therefore, if native lactate dehydrogenase is present during a fermentation in which alanine is the desired product, the lactate dehydrogenase could undesirably compete with alanine dehydrogenase.

In order to prevent lactate dehydrogenase from possibly competing with alanine dehydrogenase in the generation of the pyruvate derivative alanine, we constructed an ldhA deletion mutant of CGSC6162. In *E. coli*, ldhA is the gene that encodes lactate dehydrogenase. We also further improved the alanine production process regarding oxygenation by curtailing agitation during the course of the fermentation as suggested in Example IX. The ldhA::Kan deletion mutant from the *E. coli* strain NZN111 (Bunch et al., *Microbiology*, 143: 187-195 (1997)) was introduced into CGSC6162 by P1 phage transduction. We transformed this CGSC6162 ldhA deletion mutant with the pTrc99A-alaD plasmid that we constructed which overproduces alanine dehydrogenase from *Bacillus sphaericus*.

CGSC6162 ldhA::Kan pTrc99A-alaD cells were grown in a BioFlow 2000 fermenter (New Brunswick Scientific Co., New Brunswick, N.J.), with 1.5 L of media containing 40.0 g/L glucose, 6.0 g/L succinic acid, 3.0 g/L acetic acid, 10 g/L tryptone, 2.5 g/L yeast extract, 3.0 g/L $KH_2PO_4$, 6.0 g/L $NaH_2PO_4$, 6.0 $NH_4Cl$, 0.14 g/L $CaCl_2.2H_2O$ and 0.25 g/L $MgSO_4.7H_2O$, and 100 mg/L ampicillin. The fermenter was operated at 37° C., a pH of 7.0, with 1000 rpm agitation and 1.0 L/min air flow. After 4.0 hours of growth in the fermenter, IPTG was added to a final concentration of 1.0 mM. At 11.0 hours of growth in the fermenter, the agitation was reduced to 250 rpm. At 15.0 hours of growth in the fermenter, an additional 110 mL volume of solution was added to the fermenter containing 30 g glucose and 7.5 g $NH_4Cl$.

Figure 7:
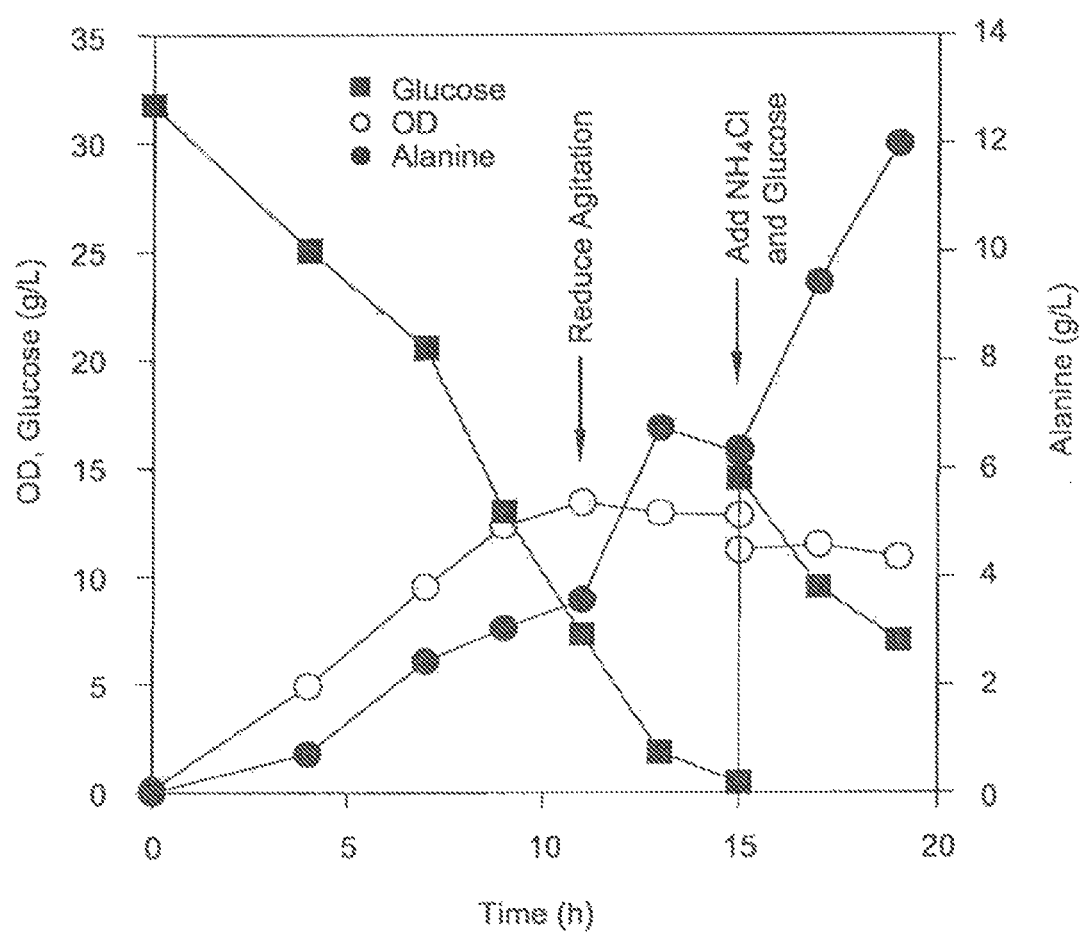
FIG. 7 shows a graph of cell growth, alanine production and glucose consumption as a function of time in a fermentation using an ldhA deletion mutant of CGSC6162 modified to overexpress the alaD gene from *B. sphaericus*.

FIG. 7 shows the results, with alanine accumulating to 12 g/L. These results show that the deletion of ldhA in CGSC6162 does not deleteriously impact cell growth. Furthermore, these results demonstrate that additional improvement in the production of pyruvate derivatives such as alanine can be attained both by genetic means (ldhA mutation) and by process modifications (optimal oxygenation).

Increased Yield with Increased Ammonium

By altering growth conditions and supplying additional ammonium chloride, the yield of alanine increased to 32 g/liter. See M. Lee et al., *Appl. Microbiol. Biotechnology* 65: 56-60 (2004).

Specifically, cells of CGSC6162 ldhA pTrc99A-alaD were first grown at 20 mL volume in an agitated screw top test tube with media composed of (per liter) 15.0 g glucose, 3.0 g acetic acid, 6.0 g succinic acid, 2.5 g tryptone, 2.5 g NaCl, and 1.25 g yeast extract. After 3 hours of growth 10 mL was used to inoculate 100 mL of media in a 250 mL baffled shake flask composed of (per liter) 15.0 g glucose, 3.0 g acetic acid, 6.0 g succinic acid, 10.0 g tryptone, 2.5 g yeast extract, 3.0 g $KH_2PO_4$, 6.0 g $Na_2HPO_4$, 6.0 g $NH_4Cl$, 0.14 g $CaCl_2.H_2O$, and 0.25 g $MgSO_4.7H_2O$. Cells were grown at 250 rpm (19 mm radius of orbit) for 6 hours and then used to inoculate a fermenter of the same composition as the shake flask except 40 g/liter glucose. Fermentations of 1.5 liter initial volume were conducted using a BioFlow 2000 (New Brunswick Scientific Company, New Brunswick, N.J.). Air was supplied continuously at 1.0 liter/minute. After 3-4 hours of growth in the fermenter, 1.0 mM isopropyl-β-D-thiogalactopyranoside (IPTG) was added for gene induction. During the first 11 hours of fermentation, the agitation was 1000 rpm, a rate which insured that the dissolved oxygen remained above 20% of saturation. At 11 hours the alanine production phase was initiated by reducing the agitation rate to a lower constant value as described in the text. Oxygen mass transfer coefficients ($k_L a$) for each experimental agitation rate were determined in a separate experiment using the static sparging method (W. S. Wise, *J. Gen. Microbiol.* 5: 167-177 (1951)) with identical media and fermenter system. At 15 hours, additional glucose and $NH_4Cl$ was added as described in the text to replenish these components that had been consumed for the generation of cell mass and alanine. All media contained 100 mg/liter ampicillin and were carried out at 37° C. and a pH of 7.0 controlled throughout the fermentations.

Figure 8A:
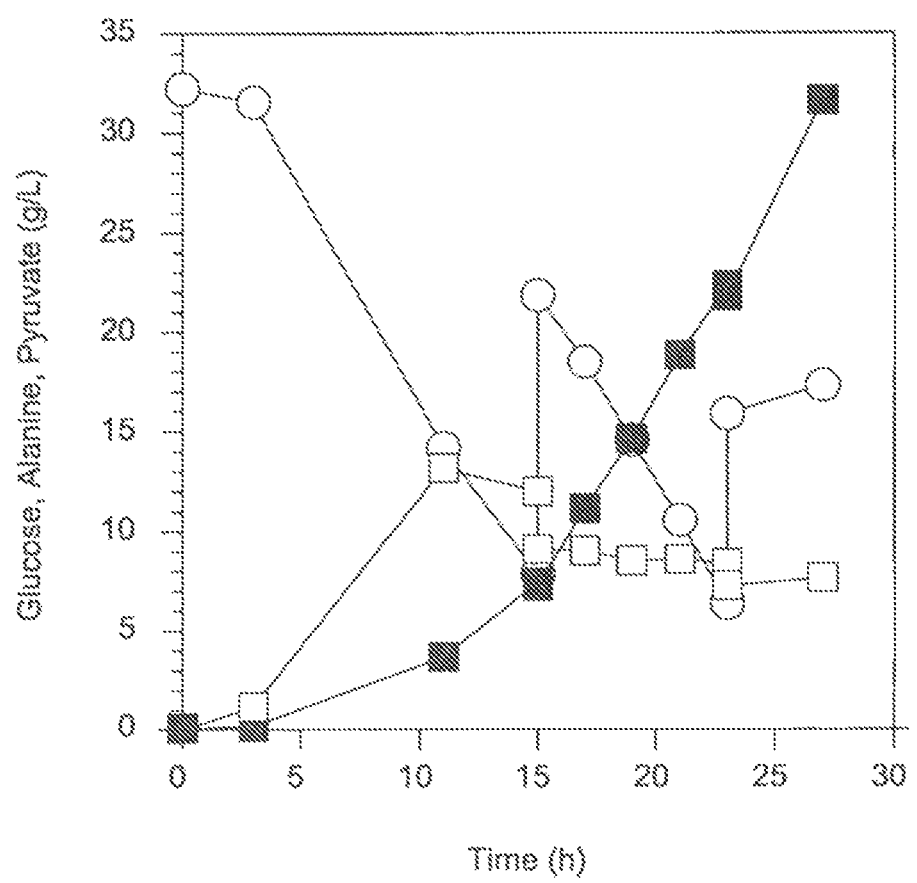
FIG. 8 shows a graph of the production of alanine in CGSC6162 ldhA pTrc99A-alaD using modified growth parameters and supplemented with additional $NH_4Cl$: (a) glucose (O), alanine (■), pyruvate (□); (b) OD (•), succinate (Δ), acetate (∇).
Figure 8B:
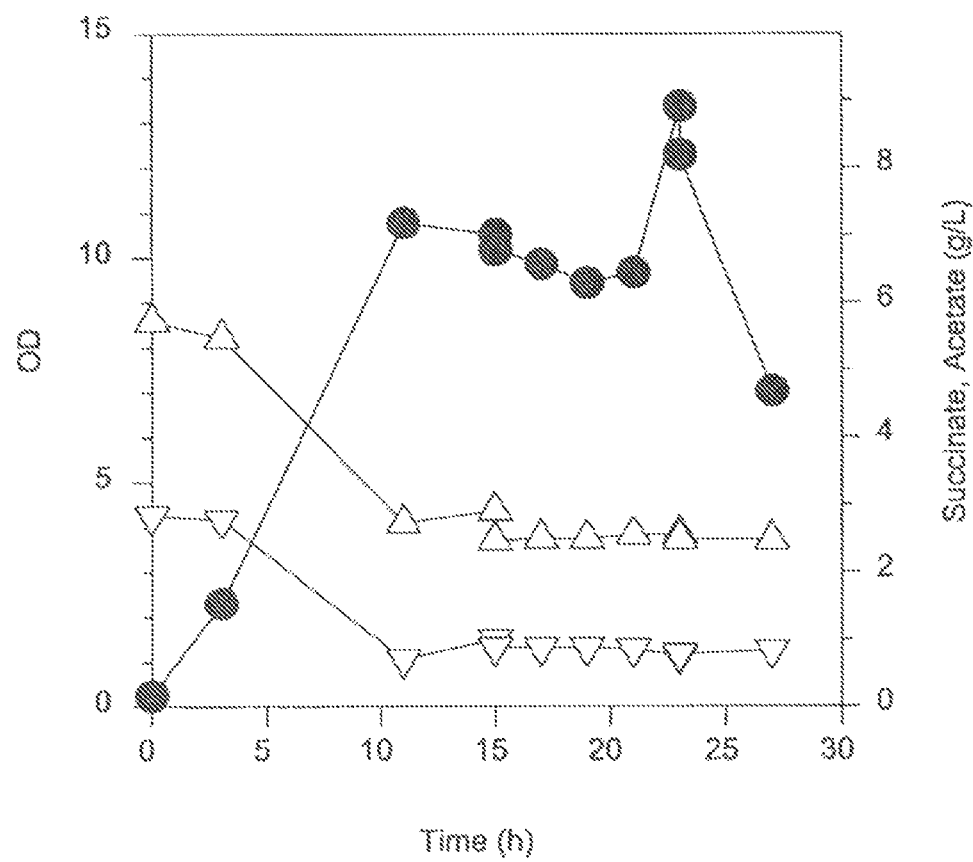

In studies on the effect of $k_L a$ on alanine accumulation, a consistent result was that alanine generation occurred at the highest rate immediately following the addition of glucose and $NH_4Cl$ at 15 hours. In order to determine whether $NH_4Cl$ was limiting the conversion of pyruvate to alanine via alanine dehydrogenase, we determined the ammonium ion concentration at the end of these fermentations, and found the ammonium concentration to be a minimum of 20 mmol/liter. We then repeated those fermentations with the lowest value of $k_L a$ of 7 hour$^{-1}$. In this case, however, we provided three times the $NH_4Cl$ (22.5 g) with the 30 g glucose at 15 hours and then both materials again at 23 hours. The resulting rate of alanine production was consistently above 2.0 g/liter hour between 15 hours and 27 hours (FIG. 8), significantly greater than previously when less $NH_4Cl$ was added. In duplicate experiments, the alanine concentration reached 32 g/liter in 27 hour, but the alanine concentration did not increase further regardless of whether additional glucose and $NH_4Cl$ was added. The overall alanine yield on glucose averaged 0.63 g/g, and the alanine yield on glucose after 15 hours averaged 0.81 g/g.

Example XI

Reduction of Pyruvate Oxidase Activity

An enzyme that can assimilate pyruvate is pyruvate oxidase. We observed significant pyruvate oxidase activity (over 1.00 IU/mg protein) after acetate was depleted in all the fed-batch fermentations operated at various levels of pH (Example V). These results suggest that reducing or eliminating pyruvate oxidase activity would prevent a portion of the pyruvate generated from being lost.

One approach is to knock out the poxB gene in *E. coli* expressing pyruvate oxidase. These strains are expected to grow and accumulate pyruvate at higher levels under the previously tested conditions.

Example XII

Conversion of Glycerol to Pyruvate by *E. coli* Using Acetate- and Acetate/Glucose-Limited Fed-Batch Processes There is an increased interest in the use of glycerol as a substrate for bioprocesses, primarily because of the increasing availability of crude material from biodiesel production. Crude glycerol might be directly suitable as a microbial feedstock, particularly for the production of low-value commodity chemicals such as succinic acid, ethanol, and propionic acid (Yazdani et al., 2007, Curr Opin Biotechnol 18:213-219). One challenge in the use of this substrate, however, lies in its lower energy value compared to glucose and other 6-carbon carbohydrates. Although per mole of pyruvate formed, glycerol generates as much ATP as glucose, more ATP is required for the biochemical formation from glycerol of several precursor molecules needed for biomass, including glucose 6-phosphate, fructose 6-phosphate, ribose 5-phosphate and erythrose 4-phosphate. Therefore, compared to glucose, the use of glycerol as a sole carbon source would be expected to result in a lower yield of pyruvate and pyruvate-derived biochemicals. One means to redirect glycerol to the desired product would be to supply a limiting amount of an energy-rich substrate, ideally one which would also generate some of the needed precursor molecules, such as glucose itself.

Pyruvic acid (pyruvate) is widely used in food, chemicals, and pharmaceuticals and as a starting material for several specialty chemicals (Li et al., 2001, Appl Microbiol Biotechnol 57:451-459). After appropriate metabolic modifications, microorganisms can produce significant quantities of pyruvate from glucose and other renewable resources (Li et al., 2001, Appl Microbiol Biotechnol 57:451-459). For example, pyruvate accumulates from the substrate glucose readily in *E. coli* strains which lack activities in the pyruvate dehydrogenase complex, pyruvate formate lyase and pyruvate oxidase (Tomar et al., 2003, Appl Microbiol Biotechnol 62:76-82; Zelic et al., 2003, Eng Life Sci 3(7):299-305). Because multiple metabolic blocks to prevent pyruvate assimilation also restrict the synthesis of the key metabolite acetyl CoA, such strains commonly also require acetate as a growth co-substrate. Providing excess glucose and controlling growth through acetate limitation is a convenient approach to maximizing the rate of glycolysis and hence pyruvate formation. A fed-batch process implementing this strategy has achieved 90 g/L pyruvate with a yield of 0.68 g/g glucose and a productivity of 2.1 g/L·h (Zhu et al., 2008, Appl. Environ. Microbiol, 74:6649-6655).

The goal of this study was to examine the use of glycerol as a substrate for the formation of pyruvate in an acetate-limited (fed-batch) bioprocess. In anticipation of reduced pyruvate yields compared to using glucose as a substrate, we also examined the addition of glucose to the medium as a means for the cells to synthesize precursor molecules in glycolysis and the pentose phosphate pathway. The envisioned process uses both acetate and glucose as limiting substrates (and hence their concentrations both remain nearly zero), while maintaining excess glycerol to maximize the rate of pyruvate formation.

We report the conversion of glycerol to pyruvate by *E. coli* ALS929 containing knockouts in the genes encoding for phosphoenolpyruvate synthase, lactate dehydrogenase, pyruvate formate lyase, the pyruvate dehydrogenase complex and pyruvate oxidase (Zhu et al., 2010, J. Ind Microbiol Biotechnol 37:307-312). As a result of these knockouts, ALS929 has a growth requirement of acetate for the generation of acetyl CoA. In steady-state chemostat experiments using excess glycerol and limited by acetate, lower growth rates favored the formation of pyruvate from glycerol (0.60 g/g at 0.10 $h^{-1}$ versus 0.44 g/g at 0.25 $h^{-1}$), while higher growth rates resulted in the maximum specific glycerol consumption rate (0.85 g/g·h at 0.25 $h^{-1}$ versus 0.59 g/g·h at 0.10 $h^{-1}$). The presence of glucose significantly improved pyruvate productivity and yield from glycerol (0.72 g/g at 0.10 $h^1$). In fed-batch studies using exponential acetate/glucose-limited feeding at a constant growth rate of 0.10 $h^{-1}$, the final pyruvate concentration achieved was about 40 g/L in 36 h. A derivative of ALS929 which additionally knocked out methylglyoxal synthase did not further increase pyruvate productivity or yield, indicating that pyruvate formation was not limited by the accumulation of methylglyoxal.

Materials and Methods

Strains.

Figure 9:
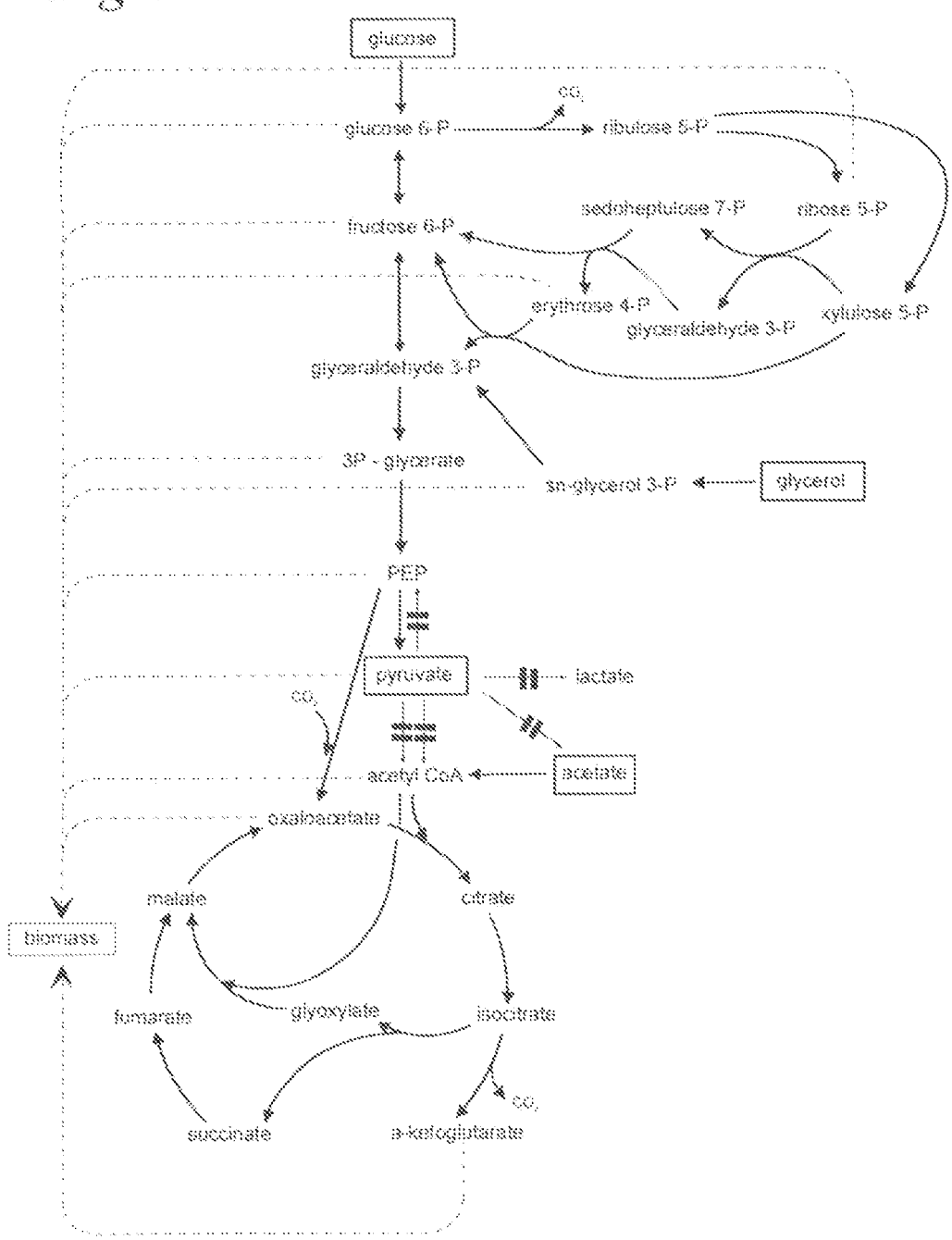
FIG. 9 shows metabolic pathways of *E. coli* ALS929 in the formation of pyruvate from glycerol and glucose. ALS929 has knockouts in genes encoding for pyruvate-formate lyase, pyruvate dehydrogenase complex, PEP synthase, pyruvate oxidase and lactate dehydrogenase (indicated by double bars). Because of these gene deletions, acetate is a required secondary substrate for the generation of acetyl CoA. Dotted lines indicate biochemical precursors from which biomass is generated.

*Escherichia coli* ALS929 (Hfr zbi::Tn10 poxB1 Δ(aceEF) rpsL pps-4 pfl-1 ldhA::Kan) (Zhu et al., 2008, Appl. Environ. Microbiol, 74:6649-6655) and ALS1115 (ALS929 mgsA::Cam) were used for this study. As a result of knockouts in genes encoding pyruvate formate lyase, the pyruvate dehydrogenase complex and pyruvate oxidase, these strains are unable to generate sufficient acetyl CoA from glucose or glycerol and therefore require acetate for growth. FIG. 9 shows the metabolic pathways for ALS929 which lead to this acetate requirement. The yccG or mgsA gene which encodes methylglyoxal synthase (Saadat et al., 1998, Biochemistry. 37:10074-10086) was knocked out using the lambda Red recombination system. Primers were designed which could amplify the chloramphenicol acetyltransferase gene and promoter from pACYC184 bracketed by the first and last 50 bases of the ppc coding sequence. The forward primer 5'-ATGTACATTATGGAACTGACGACTCG-CACTTTACCTGCGCGGAAACATAT TTGAGAAGCACACGGTCACA-3' (SEQ ID NO:1) contains the first 50 bases of the mgsA coding sequence followed by bases 3601-3620 of pACYC184 while the reverse primer 5'-TTACTTCAGACGGTCCGC-GAGATAACGCTGATAATCGGGGATCAGAATAT TACCTGTGACGGAAGATCAC-3' (SEQ ID NO:2) contains the last 50 bases of the mgsA coding sequence followed by bases 400-419 of pACYC184. The DNA from pACYC184 is underlined in the primers. The two primers were used to amplify a 1,163 bp fragment from pACYC184 DNA using the polymerase chain reaction (PCR) with Pfu polymease. The resulting DNA was gel-isolated and electroporated into DY330 electrocompetent cells which were prepared as described by Yu et al., 2000. Cam(R) colonies were then selected. The presence of the mgsA::Cam knockout was confirmed by performing PCR with the following two primer pairs which could amplify the mgsA coding sequence. The forward primer 5'-GGAACTGACGACTCGCACTT-3' (SEQ ID NO:3) contains bases 12-31 of the mgsA gene while the reverse primer 5'-TTACTTCAGACGGTCCGCGA-3' (SEQ ID NO:4) contains bases 449-468 of the mgsA gene. PCR amplification with these two primers yields a 457 bp fragment from the wild-type mgsA gene and a 1,152 bp fragment from the mgsA::Cam knockout. The mgsA::Cam knockout was then moved into ALS929 by P1 transduction.

Growth Conditions

Cells were first grown in a 250 mL shake flask containing 30 mL TYA medium for about 8 h, before transferring 5 mL to 50 mL of SF medium in a 250 mL shake flask. After 12 h of growth, the contents of this shake flask were used to inoculate a bioreactor. TYA medium contained (per L): 10.0 g tryptone, 5.0 g NaCl, 1.0 g yeast extract, 1.36 g Na($CH_3$COO).$3H_2O$. SF medium contained (per L): 10.0 g glycerol, 2.3 g Na($CH_3$COO).$3H_2O$, 5.66 g $Na_2HPO_4$.$7H_2O$, 1.5 g $KH_2PO_4$, 0.25 g NaCl, 0.5 g $NH_4$Cl, 0.1 g $MgSO_4$$7H_2O$, 0.013 g $CaCl_2$.$2H_2O$, 0.02 g thiamine.HCl, 0.5 g L-isoleucine. For chemostat experiments, the bioreactor contained carbon sources as described plus (per L): 2.51 g $K_2HPO_4$, 1.44 g $KH_2PO_4$, 0.4 g $NH_4$Cl, 4.0 g $(NH_4)_2SO_4$, 0.15 g $MgSO_4$.$7H_2O$, 0.01 g $CaCl_2$.$2H_2O$, 0.05 g $Na_2$EDTA.$2H_2O$, 0.25 mg $ZnSO_4$.$7H_2O$, 0.125 mg $CuCl_2$.$2H_2O$, 1.25 mg $MnSO_4$.$H_2O$, 0.875 mg $CoCl_2$.$6H_2O$, 0.06 mg $H_3BO_3$, 0.8859 mg $Al_2(SO_4)_3$, 0.25 mg $Na_2MoO_4$.$2H_2O$, 5.50 mg $FeSO_4$.$7H_2O$, 0.02 g thiamine.HCl, 0.2 g L-isoleucine. For fed-batch experiments, the bioreactor contained carbon sources as described plus (per L): 0.5 g $NaH_2PO_4$.$H_2O$, 0.75 g $KH_2PO_4$, 0.50 g $K_2HPO_4$.$3H_2O$, 0.2 g $NH_4$Cl, 2.0 g $(NH_4)_2SO_4$, 1.024 g $MgSO_4$.$7H_2O$, 0.01 g $CaCl_2$.$2H_2O$, 0.5 mg $ZnSO_4$.$7H_2O$, 0.25 mg $CuCl_2$.$2H_2O$, 2.5 mg $MnSO_4$.$H_2O$, 1.75 mg $CoCl_2$.$6H_2O$, 0.12 mg $H_3BO_3$, 1.772 mg $Al_2(SO_4)_3$, 0.5 mg $Na_2MoO_4$.$2H_2O$, 18.29 mg $FeSO_4$.$7H_2O$, 0.02 g thiamine.HCl, 0.75 g L-isoleucine, 10 mmol glycine betaine ("betaine"). All media contained 40 mg/L kanamycin.

Flasks were incubated at 37° C. and 250 rpm (19 mm pitch). In all bioreactor experiments, the temperature was 37° C., and the agitation at 400 rpm with an air flowrate of 1.0 L/min (Unit Instruments mass flow controllers, Orange, Calif.). Pure oxygen was supplemented as necessary to ensure that the dissolved oxygen concentration remained above 40% saturation.

Chemostat.

Continuous fermentations of 1.0 L volume operated as chemostats and were initiated in batch mode in a 2.5 L bioreactor (Bioflow 2000, New Brunswick Scientific Co. Inc. Edison, N.J., USA). The pH was maintained at 7.0 with 20% (w/v) NaOH. A steady-state condition was assumed after five residence times at which time the oxygen and $CO_2$ concentrations in the effluent gas remained unchanged. Acetate-limited chemostats at several dilution rates were conducted using 30 g/L glycerol, 1 g/L acetate and no glucose. A chemostat simultaneously limited in acetate and glucose was examined using 30 g/L glycerol, 1 g/L acetate and 2 g/L glucose. The concentrations of substrates selected ensured that the chemostats were either acetate-limited or acetate/glucose-limited. That is, in all cases acetate and glucose were essentially exhausted from the medium, while glycerol was supplied in excess. Moreover, the concentrations of acetate and glucose used generated a steady-state biomass concentration of 2-3 g/L (OD=5-6).

Fed-Batch Processes.

Fed-batch processes were carried out in a 2.5 L bioreactor (Bioflow 2000, New Brunswick Scientific Co. Edison, N.J., USA) initially containing 1.0 L medium with 20 g/L glycerol and 1 g/L acetate. Cells grew at their maximum specific growth rate (i.e., without nutrient limitation) until the initial acetate was nearly exhausted (OD about 7). At this time, the fed-batch mode commenced with a feed containing 400 g/L glycerol, 25 g/L acetate and 50 g/L glucose or with a feed containing 320 g/L glycerol and 25 g/L acetate. An exponential feed ensured that cell growth was controlled at a constant specific rate of about 0.10 h$^{-1}$. As necessary, the concentration of glycerol was adjusted in the feed to ensure that this substrate was always in excess but had not accumulated above 30 g/L. The pH was controlled at 7.0 using 5% (w/v) NH$_4$OH/ 25% KOH. Like the chemostat processes, the fed-batch processes were either acetate-limited or acetate/glucose-limited, with the concentrations of these substrates therefore generally less than detection limit of 10 mg/L during the process.

Analyses.

The optical density at 600 nm (OD) (UV-650 spectrophotometer, Beckman Instruments, San Jose, Calif.) was used to monitor cell growth, and this value was correlated to dry cell mass. Concentrations of soluble organic compounds were determined by liquid chromatography (Eiteman et al., 1997, Anal Chim Acta 338:69-75). Concentrations of oxygen and CO$_2$ in the off-gas were measured (Ultramat 23 gas analyzer, Siemens, Germany).

Results and Discussion

Formation of Pyruvate from Glycerol.

*Escherichia coli* containing the key gene mutations aceEF, ldhA, pfl, poxB, and pps, accumulates pyruvate under aerobic conditions in a glucose and acetate medium (Zelic et al., 2003, Eng Life Sci 3(7):299-305). By virtue of these mutations, the strain is unable to generate acetyl CoA from glycerol or glucose and has an absolute growth requirement for a secondary substrate which can generate acetyl CoA such as acetate (FIG. 9). However, an acetate limitation forces a high rate of glycolysis and therefore pyruvate formation (Zhu et al., 2008, Appl. Environ. Microbiol, 74:6649-6655). Glycerol should also serve as a biochemical source for pyruvate, and therefore we were interested in determining the rate of pyruvate formation from this substrate. Chemostats with *E. coli* ALS929 were used to compare dilution rates (i.e., growth rates).

We observed significant differences in process performance between the three growth rates studied: 0.10 h$^{-1}$, 0.15 h$^{-1}$ and 0.25 h$^{-1}$ (Table 1). Higher growth rates favored increased specific rates of glycerol and acetate consumption. The distribution of products changed significantly between low growth rates and high growth rates. At high growth rates, carbon was fairly evenly distributed between pyruvate and biomass: the pyruvate yield was 0.44 g/g while the biomass yield was 0.30 g/g. In contrast, over three times more pyruvate than biomass was formed at the lowest growth rate: the pyruvate yield was 0.60 g/g while the biomass yield was only 0.17 g/g. The specific CO$_2$ evolution rate was about 3 times greater at the highest growth rate than at the lowest growth rate. However, even at the highest rate of production, evolved CO$_2$ accounted for only 6.5% of the total carbon consumed.

These observations indicate that lower growth rates were much more effective in directing glycerol to the desired product pyruvate, with proportionately less biomass and CO$_2$. This conclusion is also reflected in the high ratio of glycerol-to-acetate utilization at the lowest growth rate. Cells consumed 8 mol of glycerol per mol of acetate at 0.10 h$^{-1}$ while at 0.25 h$^{-1}$ the cells consumed less than 4 mol of glycerol per mole acetate. These results can be explained in terms of the cells' maintenance requirement. In addition to generating a portion of the biomass, glycerol is converted to pyruvate to generate ATP. However, pyruvate is a biochemical "dead end" in these strains, so this biochemical accumulates. The lower the cell growth rate, the larger the fraction of the total energy demands that must be expended to fulfill the maintenance requirements. With increasing non-growth energy requirements, the cells must consume proportionately more glycerol as a means to generate that energy, leading to a higher pyruvate yield at lower growth rates. Growth rates lower than 0.10 might further increase yield, but would be less practical to control and would come at the expense of volumetric productivity. Indeed, among the growth rates studied the maximum volumetric pyruvate production rate of 0.73 g/L·h was observed at 0.15 h$^{-1}$, while the other two growth rates generated pyruvate at lower rates of 0.68 g/L·h (for 0.10 h$^{-1}$) and 0.61 g/L·h (0.25 h$^{-1}$). For these chemostat experiments the carbon recovery was consistently 78-80%.

Use of Two Limiting Substrates Simultaneously: Acetate and Glucose.

As noted the lowest growth rate studied (0.10 h$^{-1}$) resulted in the highest pyruvate yield of 0.60 g/g, although this result was still significantly lower than the maximum reported at 0.78 g/g in a similar acetate-limited process with excess glucose (Zhu et al., 2008, Appl. Environ. Microbiol, 74:6649-6655). We speculated that this lower yield was due to the demand for 4-6 carbon precursor molecules in glycolysis and the pentose phosphate pathway. We therefore conducted one additional chemostat at 0.10 h$^{-1}$ in which 2 g/L glucose was also included in the feed. Although all of the glucose could be consumed, because biomass formation was still limited by the availability of acetate, glycerol was in excess.

Several surprising results were observed in the steady-state experiment using glucose (in addition to glycerol and acetate) in the medium (Table 1). The specific rate of glycerol consumption was actually higher in the presence of glucose, and the specific rate of pyruvate production was 25% greater. Importantly, in the presence of glucose the pyruvate yield was 20% greater at 0.72 g/g. This increased yield occurred primarily because more glycerol was converted to pyruvate and at a faster rate, leading to a volumetric productivity of 1.08 g/L·h, about 60% greater than the productivity observed in the absence of glucose. Note that the increase in pyruvate generation was twice as much as the glucose that was provided: glucose addition facilitated glycerol utilization. Also, less CO$_2$ was generated in the presence of glucose, probably reflecting the diminished need for complete oxidation of substrates to meet energy requirements. Finally, over 10 mol glycerol was consumed per mol of acetate. Not only can both glycerol and glucose be consumed simultaneously, these observations suggest a relatively small quantity of glucose in the presence of glycerol can meet precursor demands for a much more effective consumption of glycerol. For this chemostat, the effluent contained no detectable acetate, about 70 mg/L glucose, and the carbon balance was 82%. We note that catabolite repression would not occur under steady-state limiting conditions because the glucose concentration remains very low (Egli et al., 1993, Ant. Leeuwen. 63; 289-298; Lendenmann et al., 1995, Microbiol. 141:71-78). Indeed, our experiments demonstrate that the presence of glucose in the feed did not reduce the specific consumption of glycerol, but in fact the inclusion of glucose actually led to a slight increase in specific glycerol consumption rate. Moreover, in the absence of glucose pyruvate was generated at a rate of 4.07 mmol/g·h, while in the presence of glucose (which was consumed at 0.44 mmol/g·h) pyruvate was generated at a rate of 5.06 mmol/g·h, a slightly higher rate than would have been obtained if all the glucose were converted to pyruvate. The inclusion of glucose also improved the overall elemental carbon yield: in the absence of glucose, 58% of (all) the carbon consumed became pyruvate whereas in the presence of glucose, 63% of the carbon consumed became pyruvate. Thus, the inclusion of glucose under limiting conditions improves the rate and yield of pyruvate production.

Although the yield of pyruvate from glycerol (0.72 g/g) compares favorably with the maximum yield from glucose previously reported in chemostat operation (0.78 g/g, Zhu et al., 2008, Appl. Environ. Microbiol, 74:6649-6655), the specific rate of pyruvate production from glycerol (0.44 g/g·h) is less than one quarter the maximum value from glucose (2.01 g/gh, Zhu et al., 2008, Appl. Environ. Microbiol, 74:6649-6655). These results highlight the slower utilization of glycerol compared to glucose as an energy-carbon source.

Fed-Batch Processes.

Figure 10:
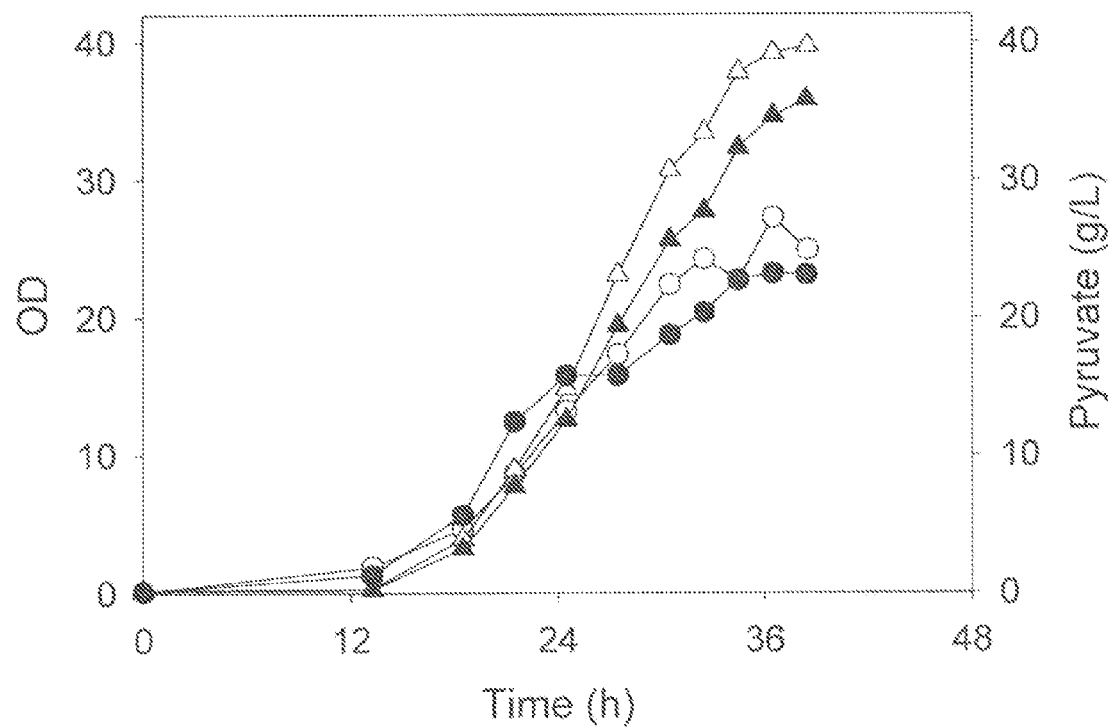
FIG. 10 shows the formation of pyruvate from glycerol in a fed-batch process at a growth rate of $0.10\ h^{-1}$ using *E. coli* ALS929 with acetate (open symbols) and with acetate and glucose (solid symbols) as limiting substrates: OD, (○,●); pyruvate, (Δ,▲). Note that the acetate and glucose concentrations were close to zero throughout the fed-batch portions of these processes. Moreover, glycerol was added as described in the Example XII to ensure that it was always present in (non-zero) excess.

Chemostat experiments provide steady-state information to assist in the design of fed-batch processes, an operational mode which allows a product to accumulate to a higher final concentration than a continuous mode. We therefore next compared two fed-batch processes using an exponential feed to maintain a specific growth rate of about $0.10\ h^{-1}$ one without glucose and a second with glucose. Similar to the chemostat experiments, growth was limited by acetate (except for a short initial time interval). Because pyruvate accumulation would simultaneously require the accumulation of $K^+$ (or another counterion) to maintain the pH, we also added the osmoprotectant betaine into the medium (Underwood et al., 2004, Appl Environ Microbiol 70:2734-40; Zhou et al., 2006, Biotechnol Lett 28:671-676). FIG. 10 shows that the results for the acetate-limited process were similar to the acetate/glucose-limited process. In both cases, cell growth slowed when the OD reached about 20 and the pyruvate concentration reached 35-40 g/L. The acetate-limited process achieved slightly higher final concentrations, with an average yield of 0.62 g/g and an average productivity of 0.88 g/L·h. The acetate/glucose-limited process consistently showed slightly lower final concentrations and the average productivity was also 0.88 g/L·h, but the yield from glycerol averaged 0.95 g/g. Similar to the observation in the chemostat studies, although a portion of the glucose could yield pyruvate, the presence of glucose improved glycerol utilization. Note that the concentrations of acetate and glucose were nearly zero throughout these nutrient-limited processes.

Although the volumetric rates and yields observed in the fed-batch process were consistent with chemostat results, we were not able to achieve pyruvate concentrations greater than 40 g/L, less than the approximately 90 g/L previously achieved from glucose (Zhu et al., 2008, Appl. Environ. Microbiol, 74:6649-6655). A significant difference between a chemostat and a fed-batch process is the greater potential for accumulation of inhibitors in the latter operational mode. We therefore speculated that an intracellular metabolite generated from glycerol might be accumulating and prevent cell growth at about an OD of about 20. One candidate inhibitor is methylglyoxal, a known potent inhibitor to *E. coli* and other cells (MacLean et al., 1998, Mol Microbiol 27:563-571). To test whether methylglyoxal accumulation was involved in the cessation of pyruvate formation in ALS929, we constructed an ALS929 derivative (denoted ALS1115) with deleted mgsA, the gene that encodes for methylglyoxal synthase. We conducted an identical fed-batch process using ALS1115 at $0.10\ h^{-1}$, and observed no change in pyruvate formation rate or final concentration (data not shown), indicating that methylglyoxal is not the source of an apparent inhibition in pyruvate formation.

In conclusion, *E. coli* ALS929 is able to accumulate pyruvate using glycerol as the substrate. Glycerol consumption, and pyruvate formation, is enhanced by the addition of glucose, which would relieve the demand for glycerol in the production of some sugar phosphates used in anabolic reactions. In a fed-batch process, pyruvate production appears to be limited to 40 g/L, perhaps as a result of the build-up of an unknown inhibitory metabolite that is not present during the conversion of glucose to pyruvate. Although the concentrations of pyruvate generated from glycerol remains below maximum concentrations observed in the same strain grown on glucose, this study highlights some potential benefits with supplementing glycerol-containing media with glucose used under growth-limitations.

REFERENCES

Baba et al., 2006, Mol Syst Biol 2:1-11.
Babaeipour et al., 2008, Biotechnol Appl Biochem 49:141-7.
Babul, 1978, J Biol Chem 253: 4350-4355.
Bunch et al., 1997 Microbiol 142:187-195.
Causey et al., 2004, 2235-2240.
Causey et al., 2003, Proc Natl Acad Sci 100(3):825-32.
Cherepanov et al., 1995 Gene 158(1):9-14.
Cotellessa et al., 2004, J Eur Acad Dermatol Venereol 18:275-278.
Datsenko et al., 2000, Proc Natl Acad Sci USA 97(12):6740-6645
Dauner et al., 2001, J Bacteriol 183(24):7308-17.
Egli et al., 1993, Ant. Leeuwen. 63; 289-298.
Eiteman et al., 1997, Anal Chim Acta 338:69-75.
Garrett et al., 1998. Biochemistry, second ed. Harcourt, Inc.
Georgellis et al., 2001, Science 292(5525):2314-2316.
Holmstrom et al., 2000, J Exp Bot 51:177-85.
Iuchi et al., 1994, J Bacteriol 176(6):1695-1701.
Koebmann et al., 2002, J Bacteriol 184:3909-3916.
Kotiarz et al., 1975, Biochim Biophys Acta. 381: 257-268.
Lee et al., 1999, Biotechnol Adv 17:29-48.
Lendenmann et al., 1995, Microbiol. 141:71-78.
Li et al., 2001, Appl Microbiol Biotechnol 57:451-459.
MacLean et al., 1998, Mol Microbiol 27:563-571.
Oliver, 2002, Nature 418:33-4.
Ono et al., 2004, J Biol Chem 279(32):33409-33412.
Roufs, 1996, Muscle and Fitness 57:195-197.
Ruyter et al., 1991, J Bacteriol 173:6184-6191.
Saadat et al., 1998, Biochemistry. 37:10074-10086.
Schaaff et al., 1989, Yeast 5:285-290.
Sorgen et al., 1998, J Biol Chem 273(43):27873-27878.
Stanko et al., 1994, Amer J Clin Nutr 59:423-427.
Stanko et al., 1990, J Appl Physiol 69:1651-1656.
Stanko et al., 1992, Amer J Clin Nutr 56:630-635.
Stanko et al., 1992, Amer J Clin Nutr 55:771-776.
Tomar et al., 2003, Appl Microbiol Biotechnol 62:76-82.
Underwood et al., 2004, Appl Environ Microbiol 70:2734-40.
VanBogelen et al., 1996, J Bacteriol 178(15):4344-66.
Vemuri et al., 2006, Appl Environ Microbiol 72:3653-61.
Wimpenny et al., 1972, J Bacteriol 111:24-32.
Yancey, 2005, J Exp Biol 208:2819-30.
Yazdani et al., 2007, Curr Opin Biotechnol 18:213-219.
Yokota et al., 1994, Appl Microbiol Biotechnol 41:638-643.
Yokota et al., 1994, Bioscience Biotechnol Biochem 58:2164-2167.
Yu et al., 2000, Proc Natl Acad Sci USA 97(11):5978-5983.
Zelic et al., 2003, Eng Life Sci 3(7):299-305.
Zelic et al., 2004, Biotechnol Bioeng 85:638-646.
Zhou et al., 2006, Biotechnol Lett 28:671-676.
Zhu et al., Appl Environ. Microbiol, 2007, 73:456-464.
Zhu et al., 2008, Appl Environ Microbiol, 74:6649-6655.
Zhu et al., 2008, Biotechnol Lett, 30:1943-1946.
Zhu et al., 2010, J. Ind Microbiol Biotechnol 37:307-312

TABLE 8

Comparison of dilution rates and limiting nutrients during chemostats of *E. coli* ALS929 with excess glycerol.

| Dilution Rate (l/h) | Limiting Nutrients | $q_{Gly}$ (g/g·h) | $q_A$ (g/g·h) | $q_{Pyr}$ (g/g·h) | $q_{Gly}:q_A$ (mol/mol) | $q_{CO2}$ (mmol/g·h) | $Y_{X/Gly}$ (g/g) | $Y_{Pyr/Gly}$ (g/g) | $Y_{Pyr/X}$ (g/g) |
|---|---|---|---|---|---|---|---|---|---|
| 0.10 | Acetate | 0.59 | 0.048 | 0.35 | 7.97 | 0.71 | 0.17 | 0.60 | 3.54 |
| 0.15 | Acetate | 0.66 | 0.068 | 0.36 | 6.27 | 0.80 | 0.23 | 0.54 | 2.39 |
| 0.25 | Acetate | 0.85 | 0.150 | 0.37 | 3.62 | 2.13 | 0.30 | 0.44 | 1.49 |
| 0.10 | Acetate + Glucose | 0.61 | 0.039 | 0.44 | 10.17 | 0.55 | 0.16 | 0.72 | 4.40 |

$q_{Gly}$: specific glycerol consumption rate
$q_A$: specific acetate consumption rate
$q_{Pyr}$: specific pyruvate productivity
$q_{CO2}$: specific carbon dioxide evolution rate
$Y_{X/Gly}$: mass yield coefficient of biomass/glycerol
$Y_{Pyr/Gly}$: mass yield coefficient of pyruvate/glycerol
$Y_{Pyr/X}$: mass yield coefficient of pyruvate/biomass The complete disclosures of all patents, patent applications including provisional patent applications, and publications, and electronically available material (e.g., GenBank and Protein Data Bank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A bacterial cell for use in making a metabolite comprising pyruvate or a pyruvate derivative, the bacterial cell exhibiting reduced activity of at least one enzyme in the pyruvate dehydrogenase (PDH) complex of enzymes, compared to a wild-type bacterial cell; wherein the bacterial cell is capable of accumulating the metabolite to a concentration of at least about 3.3 g/L when cultured in the presence of glucose and at least one of acetate and succinate.

2. The bacterial cell of claim 1 which is an *E. coli* cell.

3. The bacterial cell of claim 1 further exhibiting added or increased NADH oxidase activity compared to a wild-type bacterial cell.

4. The bacterial cell of claim 1 further exhibiting reduced activity of at least one of phosphoenolpyruvate carboxylase (PEP carboxylase) and pyruvate oxidase compared to a wild-type bacterial cell.

5. The bacterial cell of claim 1 further exhibiting added or increased acetolactate synthase activity compared to a wild-type bacterial cell.

6. The bacterial cell of claim 1 further exhibiting added or increased alanine dehydrogenase activity compared to a wild-type bacterial cell.

7. The bacterial cell of claim 1 further exhibiting an increase in the amount of NAD, or the rate at which NAD is regenerated, compared to a wild-type bacterial cell.

8. The bacterial cell of claim 1 wherein pyruvate dehydrogenase (PDH) activity is undetectable.

9. The bacterial cell of claim 1 wherein a gene encoding at least one enzyme in the pyruvate dehydrogenase (PDH) complex of enzymes is knocked out.

* * * * *